US011701272B2

(12) United States Patent
Roldan-Posada et al.

(10) Patent No.: US 11,701,272 B2
(45) Date of Patent: *Jul. 18, 2023

(54) ABSORBENT ARTICLE WITH IMPROVED FECAL MATTER CONTAINMENT FLAPS

(71) Applicant: Kimberly-Clark Worldwide, Inc., Neenah, WI (US)

(72) Inventors: Carlos E. Roldan-Posada, Medellin (CO); Andrea F. Orifici, Olavarría (AR); Juliana Restrepo, London (GB)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 215 days.

This patent is subject to a terminal disclaimer.

(21) Appl. No.: 17/147,828

(22) Filed: Jan. 13, 2021

(65) Prior Publication Data

US 2021/0177667 A1 Jun. 17, 2021

Related U.S. Application Data

(63) Continuation of application No. 16/318,894, filed as application No. PCT/US2016/044652 on Jul. 29, 2016, now Pat. No. 10,918,535.

(51) Int. Cl.
| | |
|---|---|
| *A61F 13/494* | (2006.01) |
| *A61F 13/514* | (2006.01) |
| *A61F 13/49* | (2006.01) |

(52) U.S. Cl.
CPC .. *A61F 13/49406* (2013.01); *A61F 13/51496* (2013.01); *A61F 13/49007* (2013.01); *A61F 2013/4944* (2013.01)

(58) Field of Classification Search
CPC .............. A61F 13/49007; A61F 13/494; A61F 13/49406; A61F 13/51496; A61F 2013/4944
See application file for complete search history.

(56) References Cited

U.S. PATENT DOCUMENTS

| | | | |
|---|---|---|---|
| 4,695,278 | A | 9/1987 | Lawson |
| 4,704,115 | A | 11/1987 | Buell |
| 4,892,536 | A | 1/1990 | DesMarais et al. |
| 4,990,147 | A | 2/1991 | Freeland |
| 5,176,672 | A | 1/1993 | Bruemmer et al. |
| 5,397,318 | A | 3/1995 | Dreier |

(Continued)

FOREIGN PATENT DOCUMENTS

| | | |
|---|---|---|
| CN | 1213958 A | 4/1999 |
| CN | 101212945 A | 7/2008 |
| WO | 0000226 A1 | 1/2000 |

*Primary Examiner* — Michele M Kidwell
(74) *Attorney, Agent, or Firm* — Kimberly-Clark Worldwide, Inc.

(57) ABSTRACT

An absorbent article can include a chassis including an absorbent body. The chassis can include a body facing surface. The absorbent article can also include a pair of body exudate containment flaps attached to the body facing surface of the chassis. The containment flaps can include a first portion located in the front portion of the absorbent article and chassis, and a second portion located in the rear portion of the absorbent article and chassis. The second portion of the containment flaps can have one or more properties that are different than one or more properties of the first portion of the containment flaps to reduce the lateral flow of body exudates out the sides of the absorbent article.

20 Claims, 15 Drawing Sheets

(56) References Cited

U.S. PATENT DOCUMENTS

| | | |
|---|---|---|
| 5,413,570 A | 5/1995 | Enloe |
| 5,514,121 A | 5/1996 | Roe et al. |
| 5,531,730 A | 7/1996 | Dreier |
| H1630 H | 1/1997 | Roe et al. |
| 5,620,431 A | 4/1997 | LeMahieu et al. |
| 5,624,426 A | 4/1997 | Roe et al. |
| 5,810,800 A | 9/1998 | Hunter et al. |
| 5,931,826 A | 8/1999 | Faulks et al. |
| 5,957,907 A | 9/1999 | Sauer |
| 5,993,433 A | 11/1999 | St. Louis et al. |
| 6,010,491 A | 1/2000 | Roe et al. |
| 6,017,336 A | 1/2000 | Sauer |
| 6,022,338 A | 2/2000 | Putzer |
| 6,102,892 A | 8/2000 | Putzer et al. |
| 6,117,121 A | 9/2000 | Faulks et al. |
| 6,121,510 A | 9/2000 | Sauer |
| 6,280,426 B1 | 8/2001 | Turner et al. |
| 6,494,872 B1 | 12/2002 | Suzuki et al. |
| 6,497,693 B1 | 12/2002 | Otsubo |
| 6,508,798 B1 | 1/2003 | Widlund et al. |
| 6,595,972 B1 | 7/2003 | Wise et al. |
| 6,699,228 B1 | 3/2004 | Chmielewski et al. |
| 6,706,030 B1 | 3/2004 | Okuda et al. |
| 6,786,895 B1 | 9/2004 | Schmitz |
| 7,654,993 B2 | 2/2010 | Arizti et al. |
| 7,749,210 B2 | 7/2010 | Mishima et al. |
| 7,763,004 B2 | 7/2010 | Beck et al. |
| 7,771,408 B2 | 8/2010 | Mueller et al. |
| 7,785,309 B2 | 8/2010 | Van Gompel et al. |
| 7,794,441 B2 | 9/2010 | Ashton et al. |
| 8,043,275 B2 | 10/2011 | Peterson |
| 8,079,994 B2 | 12/2011 | Richlen et al. |
| 8,277,431 B2 | 10/2012 | Arizti et al. |
| 8,348,917 B2 | 1/2013 | Beckman et al. |
| 8,939,957 B2 | 1/2015 | Raycheck et al. |
| 10,159,610 B2 | 12/2018 | Barnes |
| 2001/0003153 A1 | 6/2001 | Sayama et al. |
| 2002/0016122 A1 | 2/2002 | Curro et al. |
| 2004/0147889 A1 | 7/2004 | Roe et al. |
| 2004/0162538 A1 | 8/2004 | Mueller et al. |
| 2005/0215972 A1 | 9/2005 | Roe et al. |
| 2007/0093771 A1 | 4/2007 | Arizti et al. |

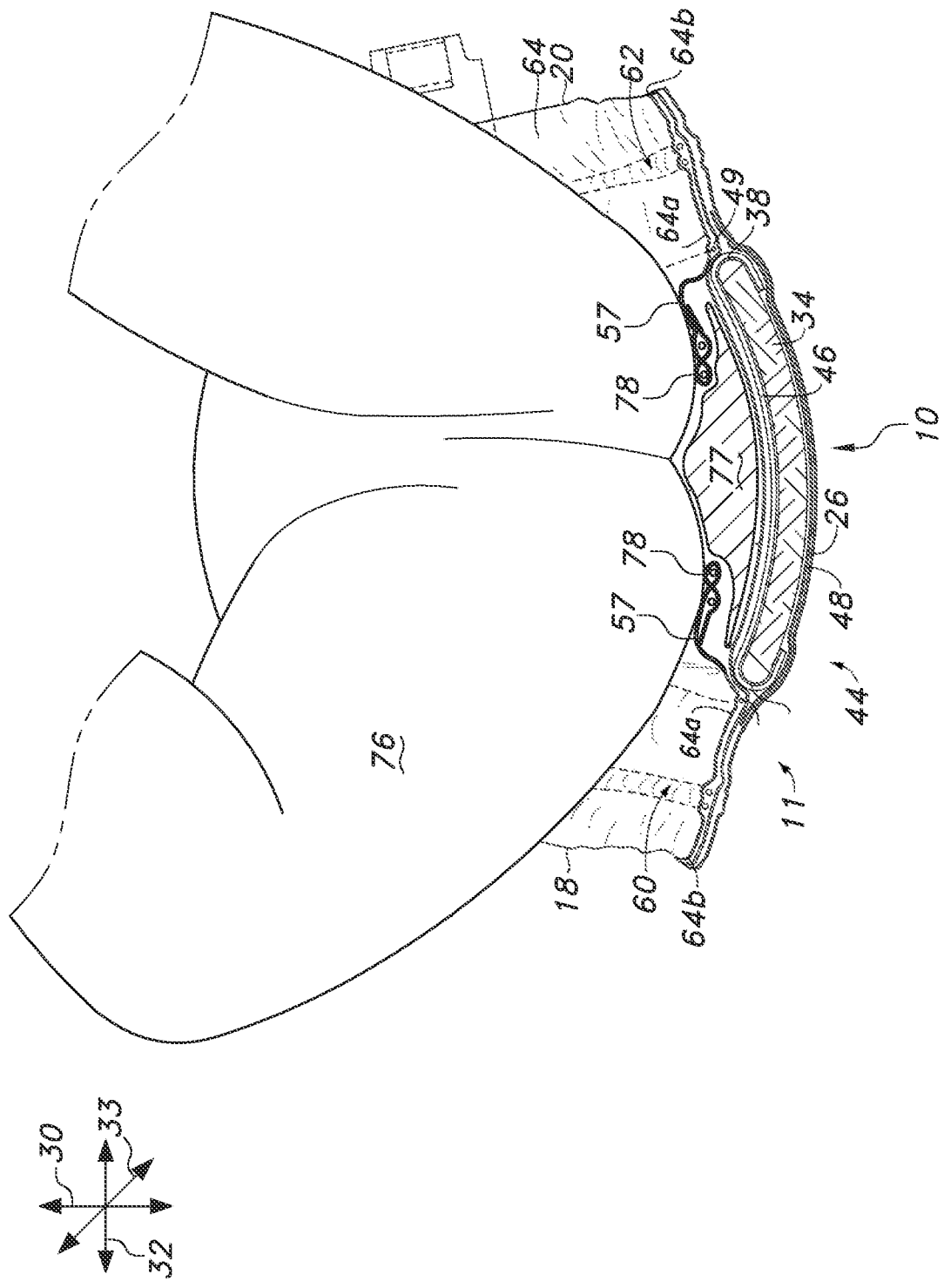

ABSORBENT ARTICLE WITH IMPROVED FECAL MATTER CONTAINMENT FLAPS

The present application is a continuation application and claims priority to U.S. patent application Ser. No. 16/318,894, filed on Jan. 18, 2019, which is a national-phase entry, under 35 U.S.C. § 371, of PCT Patent Application No. PCT/US16/44652, filed on Jul. 29, 2016, all of which are incorporated herein by reference.

TECHNICAL FIELD

The present disclosure relates to absorbent articles.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

Another important emphasis of some absorbent articles is to draw and retain exudates away from the wearer's skin. Drawing away and storing the exudates away from the wearer's skin can help to keep the skin dry and to ensure that there is minimal exposure of irritants in the exudates to the skin. These functions can help to promote and maintain healthy skin for the wearer.

One common mode of failure is for exudates to leak out of the leg and waist openings of the personal care absorbent article. The waist areas are commonly fitted with elastics waistbands. The leg areas are also commonly fitted with elastics adjacent the peripheral openings. It is known that these leg elastics in and of themselves do not provide adequate leakage protection adjacent the leg openings of the absorbent article. As a result, in addition to and inboard of the leg elastics, such articles are fitted with what are termed bowel movement (BM) containment flaps. See for example, U.S. Pat. No. 4,704,116 to Enloe of Kimberly-Clark Worldwide Inc. The function of the BM flaps is to restrain the lateral flow of both urine and feces before they come in contact with the leg elastics adjacent the leg openings of the article.

The ability of such articles to constrain feces will depend on both the age and the health of the baby, in addition to diet. As a baby transitions from milk or formula to more solid foods, BMs will generally increase in viscosity. This transition may generally occur between 3 and 9 months of age. After this transition, BMs will generally maintain a thicker consistency, with variations depending on diet, sickness, and hydration.

With pasty BMs, it has been found that conventional BM containment flaps, such as disclosed in the aforementioned Enloe reference, have particular difficulty in containing the discharged exudate. They have been found to not have a sufficient seal between the skin of the wearer and the surface of the containment flap. As a result, due to the consistency of the BM, it is possible for the BM to push the flaps laterally outward thereby further expanding the exposed surface area being soiled and not allowing the BM to be drawn away from the wearer's skin under the BM flaps. Additionally, the consistency of the BM may sometimes infiltrate between the flap and wearer's skin again causing further expansion of the soiled area of the skin and facilitating leakage out the leg openings of the article.

Numerous attempts have been made to deal with such leakage problems. In addition, the designs of such personal care absorbent articles have been modified to include additional features such as pockets and openings in the bodyside surface of the article to create additional chambers and spaces within the article to collect and separate the fecal matter from the skin of the user so there is less material which can find its way to the leg openings. Despite these variations to basic absorbent article designs, there is still a need for a design that will adequately contain fecal matter and in particular pasty BMs.

SUMMARY OF THE DISCLOSURE

The absorbent article disclosed herein is designed to improve the containment of bowel movements or BMs and in particular leakage associated with absorbent articles used with pasty BMs as well as reducing exposure of the wearer's skin to the voided BM. In this regard, the absorbent article according to the present disclosure is fitted with a pair of BM containment flaps each of which has a first portion located in the front end of the article and a second portion located in the rear end of the article with the second portion having one or more different properties from the first portion. As a result, the second portion of the containment flaps is able to provide an improved seal between the flap body facing surface and the skin of the buttocks of the wearer which in turn provides for better BM containment than conventional absorbent articles fitted with conventional containment flaps. Additionally, the improved flaps are better at maintaining their positioning on the wearer's buttocks, resisting lateral movement during a BM, and are therefore able to maintain a greater coverage over the wearer's buttocks to reduce the exposure of the wearer's skin to the BM.

In one embodiment the absorbent article can include a chassis having a front end section with a front waist region including a front waist edge and a rear end section having a rear waist region including a rear waist edge. The front waist region and rear waist region are joined by a crotch region. The chassis includes an absorbent body, with the chassis further including a body facing surface. The absorbent article defines a longitudinal axis, a lateral axis located midway between the front waist edge and the rear waist edge and the absorbent article further defines a vertical axis. The chassis is fitted with a pair of containment flaps attached to the body facing surface of the chassis. Each of the pair of containment flaps has a proximal edge adjacent and attached to the body facing surface of the chassis, the bodyside liner in one embodiment, and a distal edge joined to the proximal edge by a medial section. Each of the containment flaps defines a length and has a first end and a second end with the first end being located in the front waist region and the second end being located in the rear waist region. Each of the containment flaps has a first portion at least a portion of which is located in the front waist region of the absorbent article and a second portion at least a portion of which is located in the rear waist region of the absorbent article. Each of the containment flaps has at least one property with the at least one property in the second section being different from the at least one property in the first portion of the same containment flap.

The property in the aforementioned paragraph can include one or a combination of or more properties including, but not limited to, basis weight, elongation force, bending stiffness, coefficient of friction, flap height, flap thickness and visual distinctiveness.

BRIEF DESCRIPTION OF DRAWINGS

A full and enabling disclosure thereof, directed to one of ordinary skill in the art, is set forth more particularly in the remainder of the specification, which makes reference to the appended figures in which:

FIG. 6A is a partial perspective view of an absorbent article according to the present invention being worn and positioned adjacent a child's buttocks and the protection provided during the soiling of the absorbent article by the child.

Figure 1:
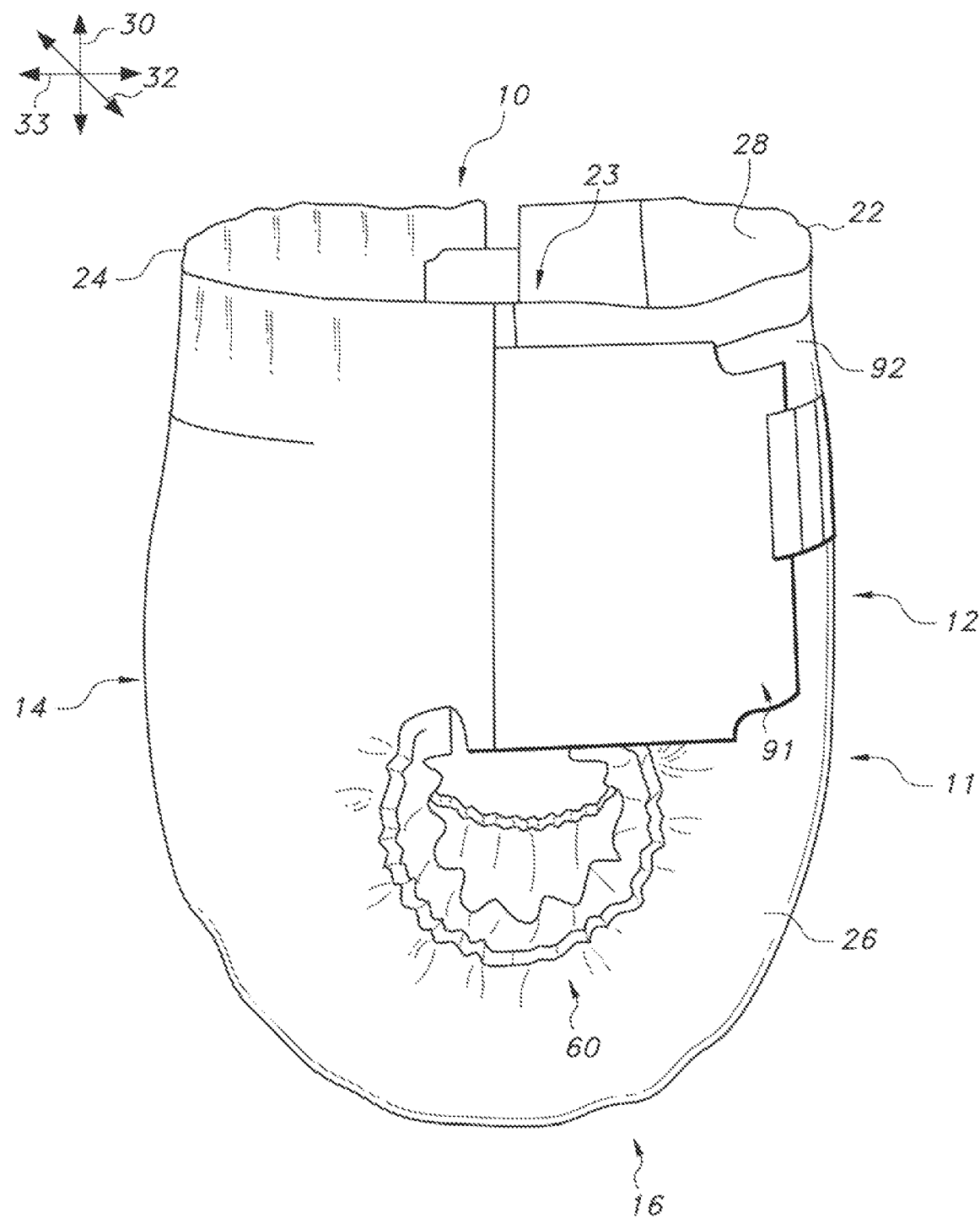
FIG. 1 perspective view of an absorbent article according to the present invention with BM containment flaps with a first portion adjacent the front waist portion of the article and a second portion adjacent the rear waist portion of the product.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article having improved bowel movement (BM) containment flaps for improved control of bowel movements and in particular pasty BMs which are commonly encountered with babies. The articles of the present disclosure may have an enhanced ability to draw away feces from the wearer's skin and to retain the feces within portions of the article away from the wearer's skin. Generally, young babies tend to have runny or liquid-y feces while they are fed exclusively breast milk or formula. As babies transition to more solid foods, their BMs become thicker, having a high consistency or viscosity. These more viscous BMs can be difficult to retain within the article and at desired locations within the article. The improved BM flaps of the present disclosure enhance the ability of the article at least in these areas.

Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions:

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, adult diapers and pants, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded", "attached" or "coupled" refers herein to the joining, adhering, connecting, attaching, or the like, of two elements. Two elements will be considered bonded, attached or coupled together when they are joined, adhered, connected, attached, or the like, directly to one another or indirectly to one another, such as when each is directly bonded to intermediate elements. The bonding, attaching or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer liquids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, hydroentangling processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "stretch film laminate" refers herein to a laminate of an elastic film laminated to at least one outer layer of fibrous nonwoven web material. Desirably, the elastic film is air and vapor permeable and liquid impermeable and elastic in at least one and preferably two directions generally perpendicular to one another. More desirably, the elastic film is elastic in all directions of the X-Y plane of the material. In other embodiments, the elastic film can have cover layers, such as fibrous nonwoven web materials laminated to both sides of the elastic film so as so form a laminate with opposed exterior nonwoven layers, an intermediate layer of elastic film bonded to both of the exterior nonwoven layers. Further information can be found with reference to U.S. Pat. No. 7,803,244 to Siqueira et al. and U.S. Pat. No. 8,361,913 to Siqueira et al., each of which is incorporated herein in its entirety by reference.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Absorbent Article:

FIGS. 1 through 7 depict an absorbent article according to the present invention. A key element of the present invention is the unique nature of the BM containment flaps (also referred to herein as simply "containment flaps" or "flaps" or "BM flaps") and the fact that the portion of the BM flaps in the rear portion of the absorbent article, in this case a diaper, are different than the portion of the BM flaps located in the front portion of the absorbent article. It has been found that this difference in the design and in the properties of the BM flaps in the rear portion of the absorbent article greatly improves the ability of the article to maintain a seal with respect to the BM flaps and the wearer such that BMs, and in particular pasty BMs, flow laterally underneath the BM flaps instead of pushing the BM flaps outward. This improved flow control of the BMs allows the articles of the present disclosure to maintain a smaller exposed skin area to the BM, thereby helping to maintain the healthiness of the skin after a BM.

Figure 6:
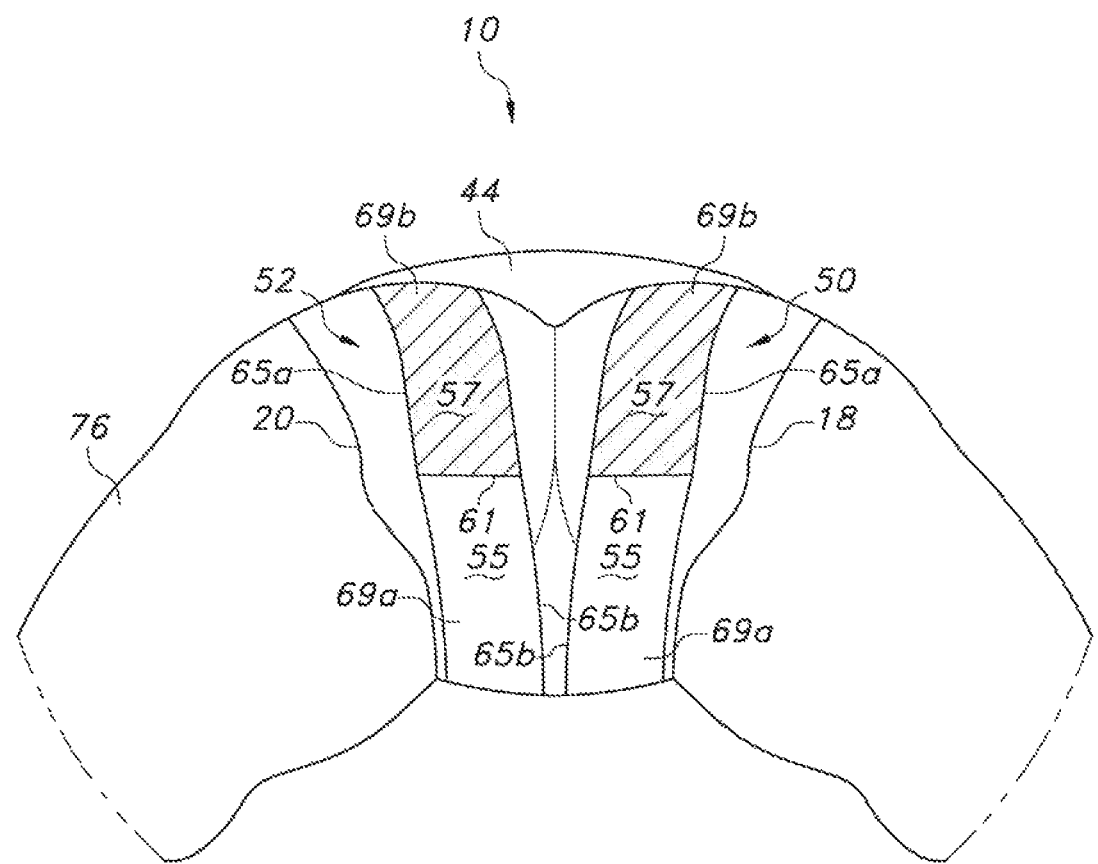
FIG. 6 is the absorbent article of FIG. 5 in a partial cutaway view with the absorbent chassis including the backsheet, absorbent core and topsheet or liner removed showing the BM containment flaps in contact with the torso.
Figure 7:
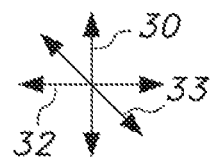
FIG. 7 is the torso of FIG. 6 with the absorbent article removed from the torso showing the stain pattern on the torso after having been soiled while wearing an absorbent article according to the present invention.
Figure 7:
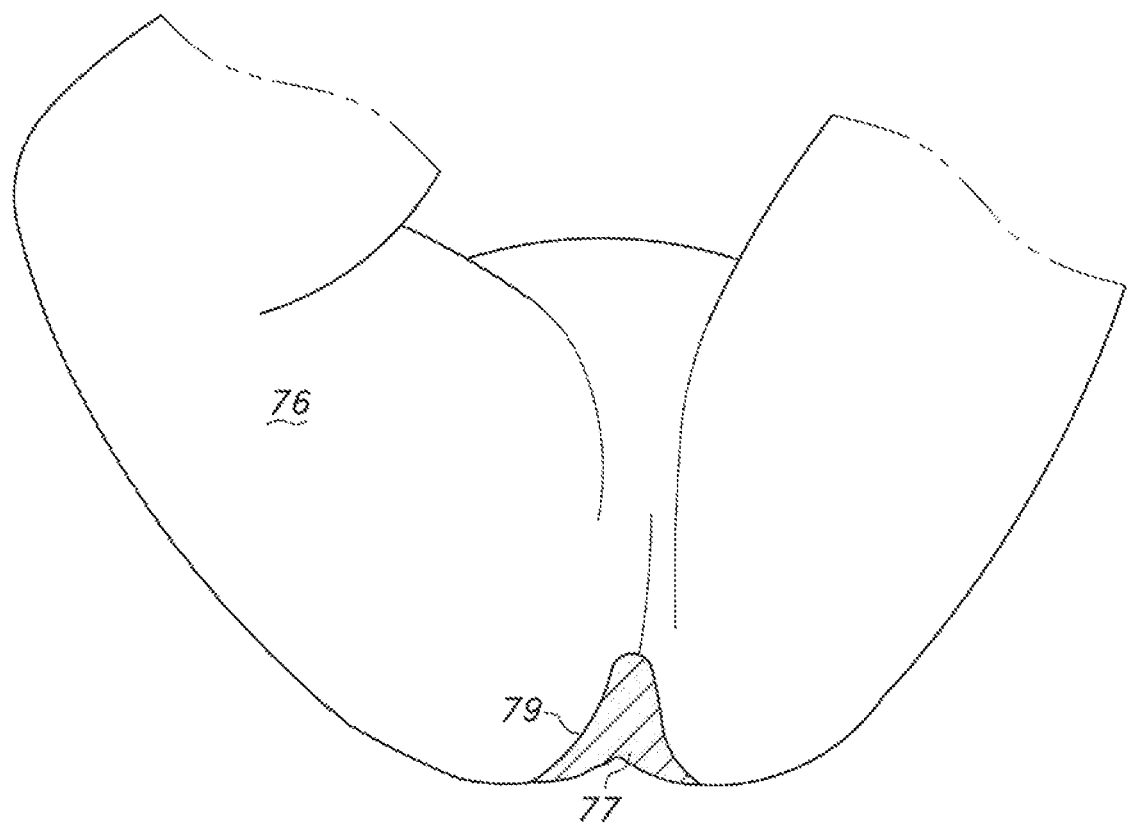
Figure 8:
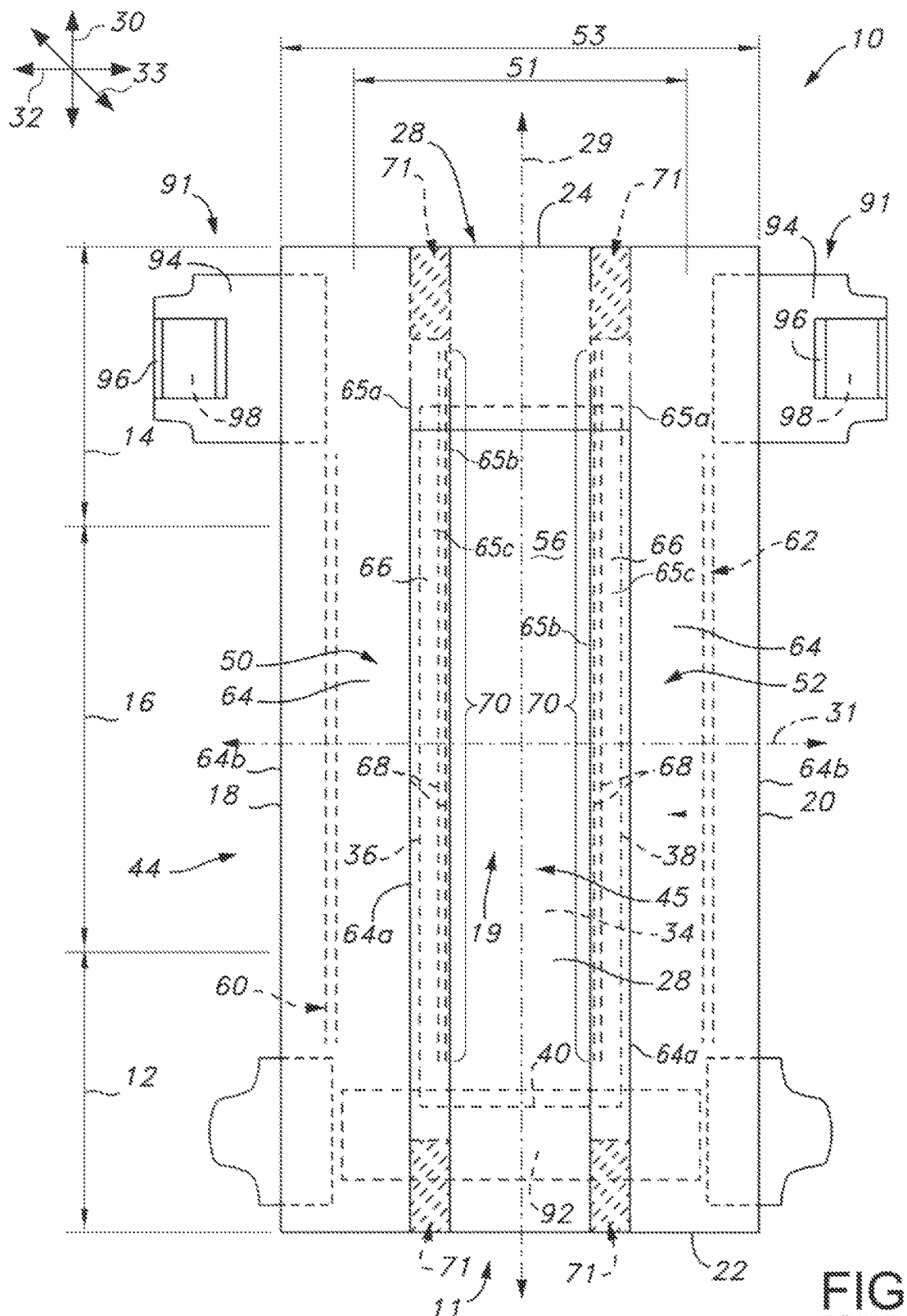
FIG. 8 is a top plan view conventional absorbent article with conventional BM flaps in a stretched, laid flat and unfastened condition.
Figure 9:
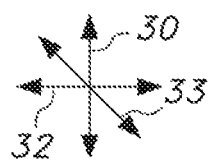
FIG. 9 is a view similar to FIG. 6 but with the conventional absorbent article of FIG. 8.
Figure 9:
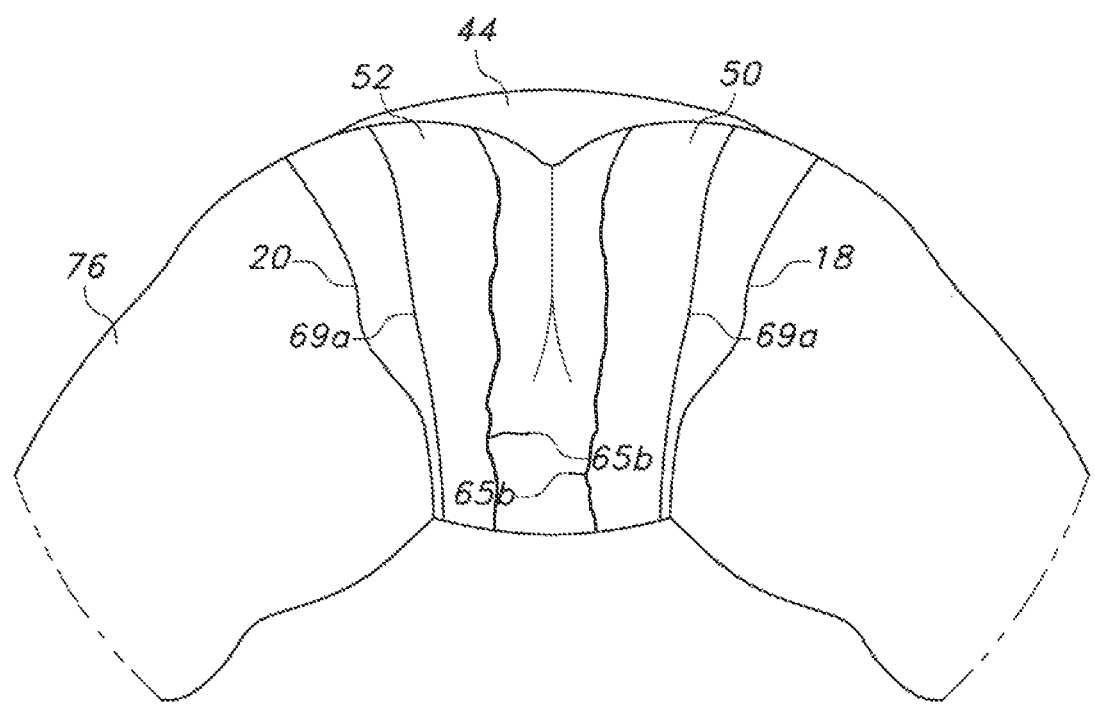
Figure 10:
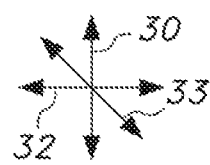
FIG. 10 is a view similar to FIG. 7 but with the conventional absorbent article of FIG. 8.
Figure 10:
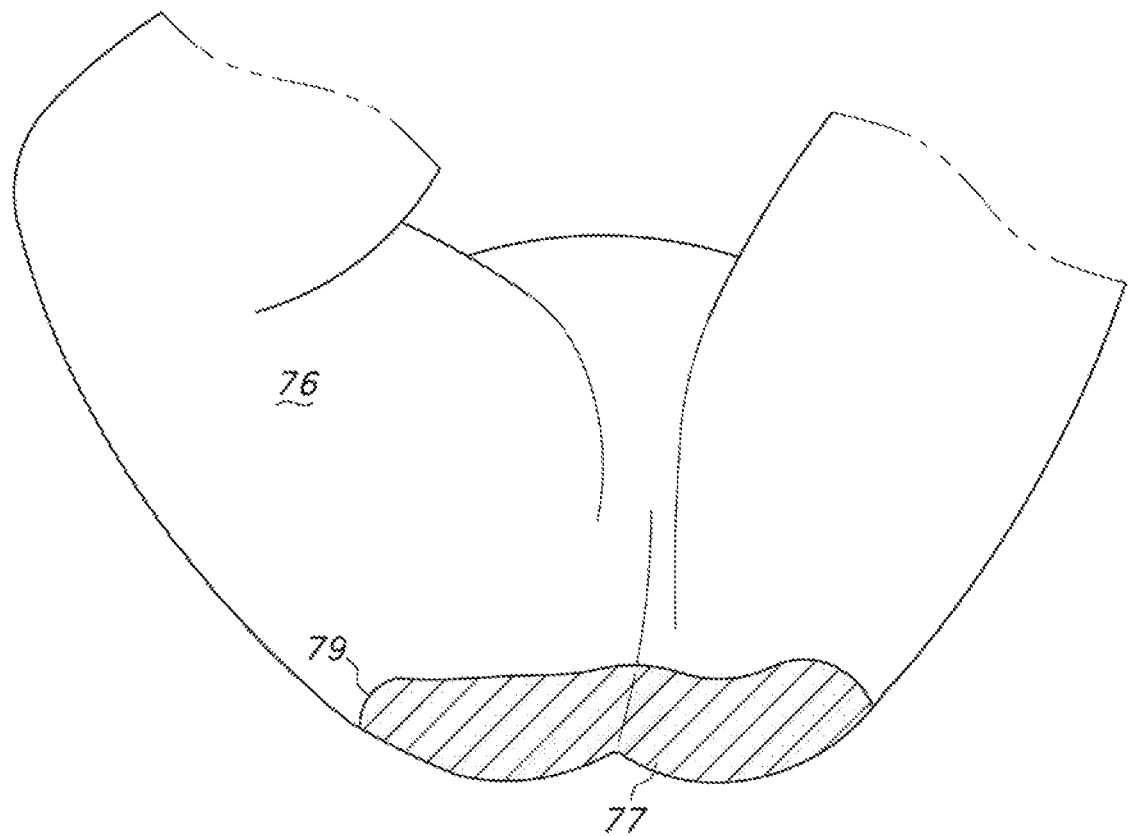

In contrast, FIGS. 8 through 10 show a conventional absorbent article, again in this case a diaper, with conventional BM flaps which are not as effective in controlling the lateral movement of BM towards the leg openings of the article. A comparison of FIGS. 6 and 7 with FIGS. 9 and 10 illustrate the improvement in the containment of the BM and the reduced area on the wearer soiled by the BM (FIG. 7 versus FIG. 10).

Figure 11:
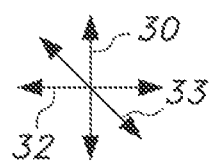
FIG. 11 is a perspective view of a conventional absorbent article fitted to a torso representing a child in a partially bent over (from the waist) configuration similar to that shown in FIG. 6 with BM containment flaps made solely from material similar to the second portion of the BM containment flaps of FIG. 1 showing the BM containment flaps crossing one another in the crotch region.
Figure 11:
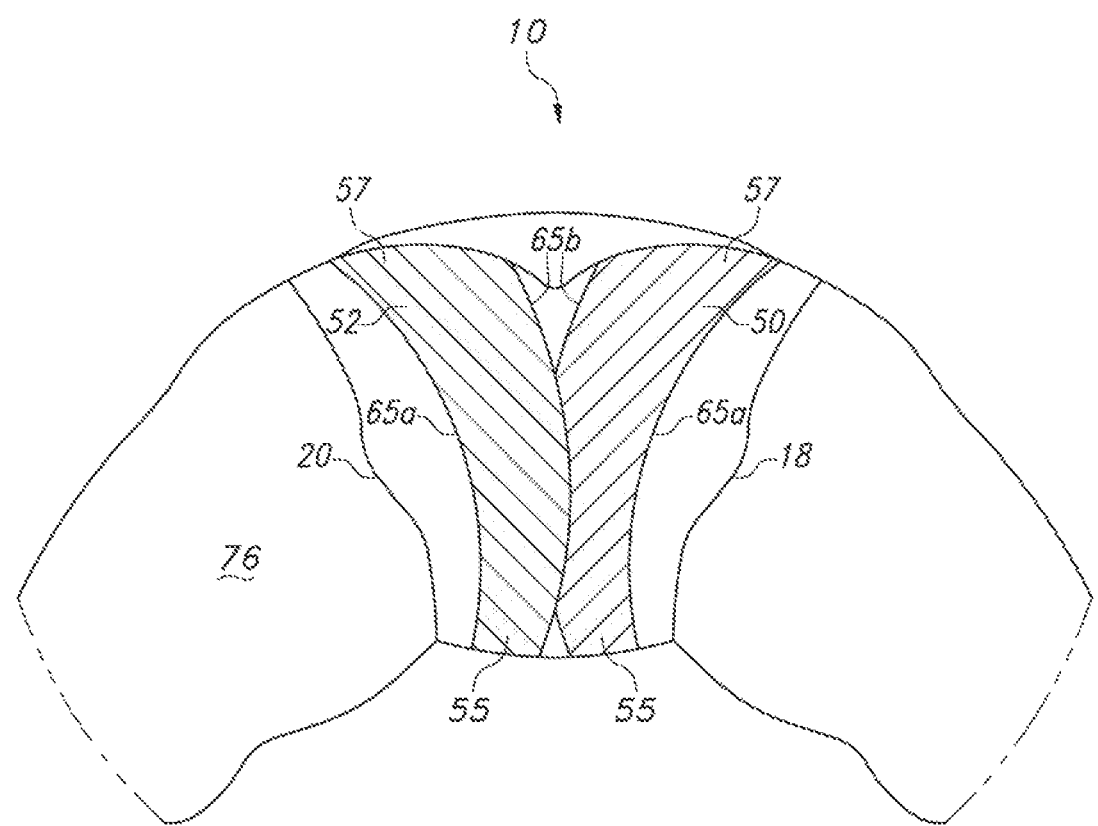

The importance of there being a difference in the construction and properties of the BM flaps in the rear portion of the absorbent article as opposed to the front portion is illustrated in FIG. 11. The absorbent article in this Figure is constructed with the BM flaps being made completely from the material used in the rear portion of the articles shown in FIGS. 1 through 7. As will be explained in greater detail below, with this embodiment an undesirable crossing effect results such that the BM flaps began to impinge upon one another in the crotch region of the absorbent article and in some cases to the point that they overlap with one another. This can interfere with the movement of the BM and urine down onto and into the absorbent structure of the absorbent article chassis. This phenomenon can be further exacerbated by the fact that in many commercial embodiments, the BM flaps are made to be liquid impermeable which means body exudates can pool on the body contacting surface of the flaps thereby compounding the inability to transport such exudates away from contact with the skin of the user.

Figure 1A:
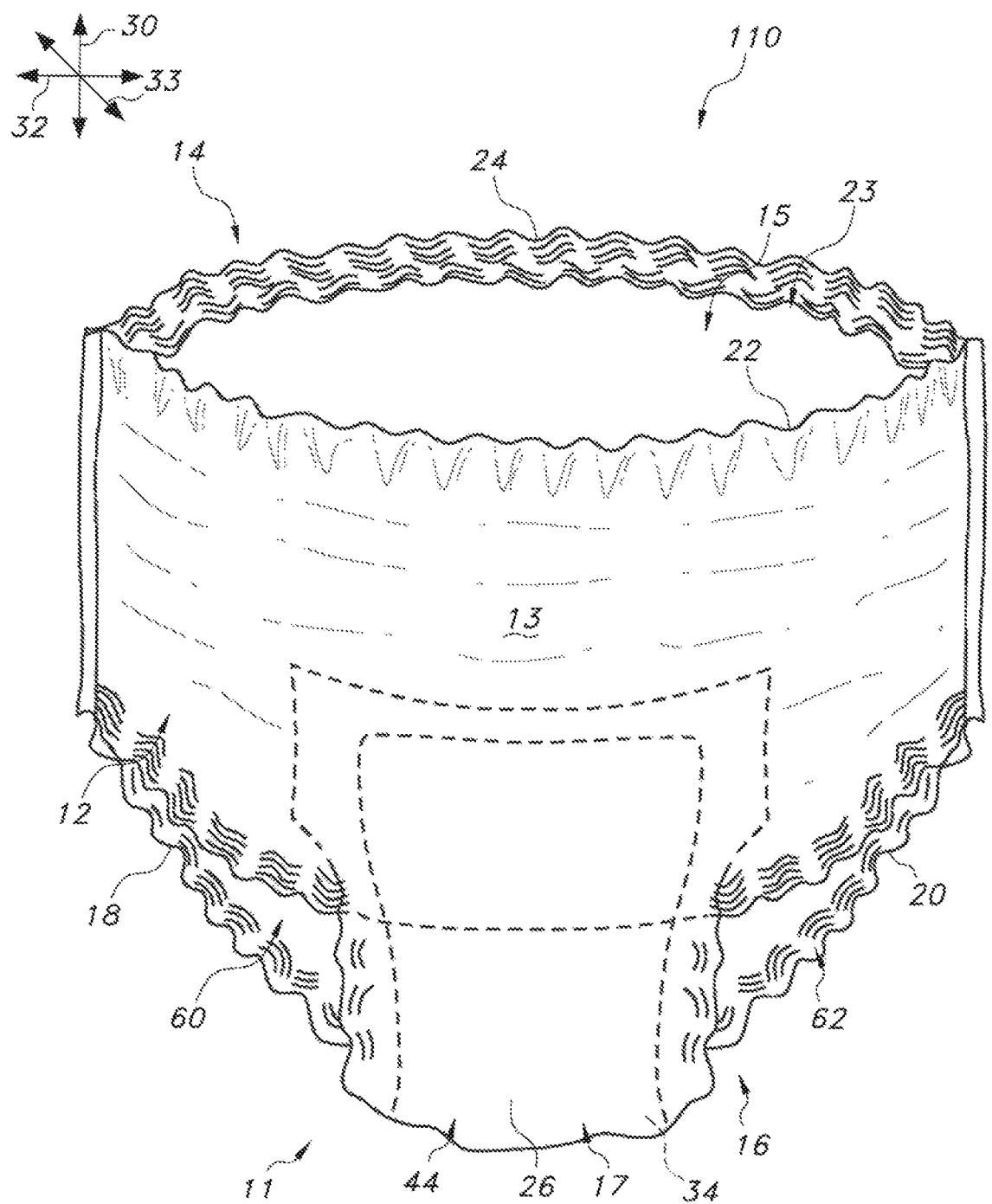
FIG. 1A perspective view of a different absorbent article according to the present invention with BM containment flaps with a first portion adjacent the front waist portion of the article and a second portion adjacent the rear waist portion of the product.
Figure 2:
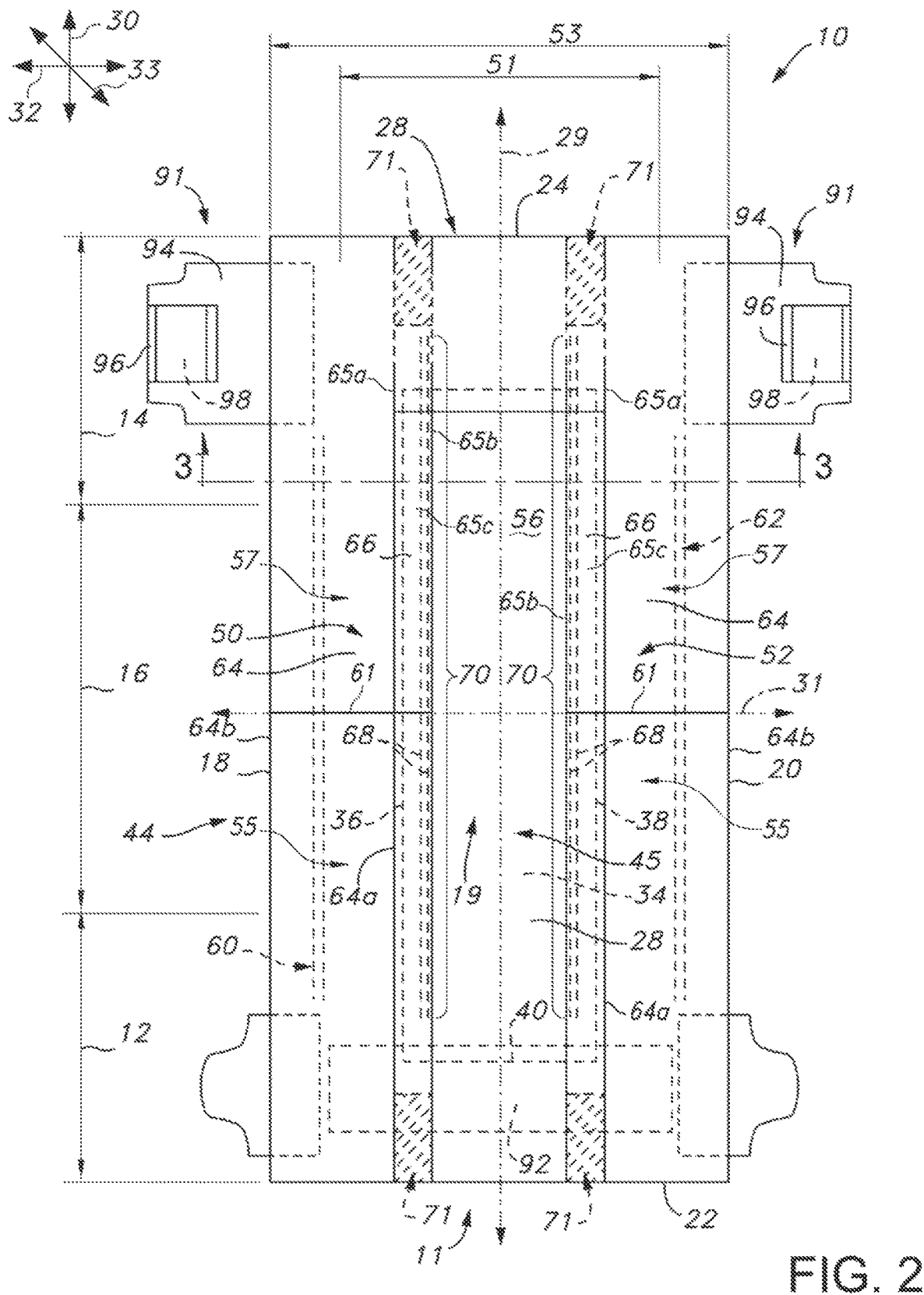
FIG. 2 is a top plan view of the absorbent article of FIG. 1 in a stretched, laid flat and unattached condition.
Figure 2A:
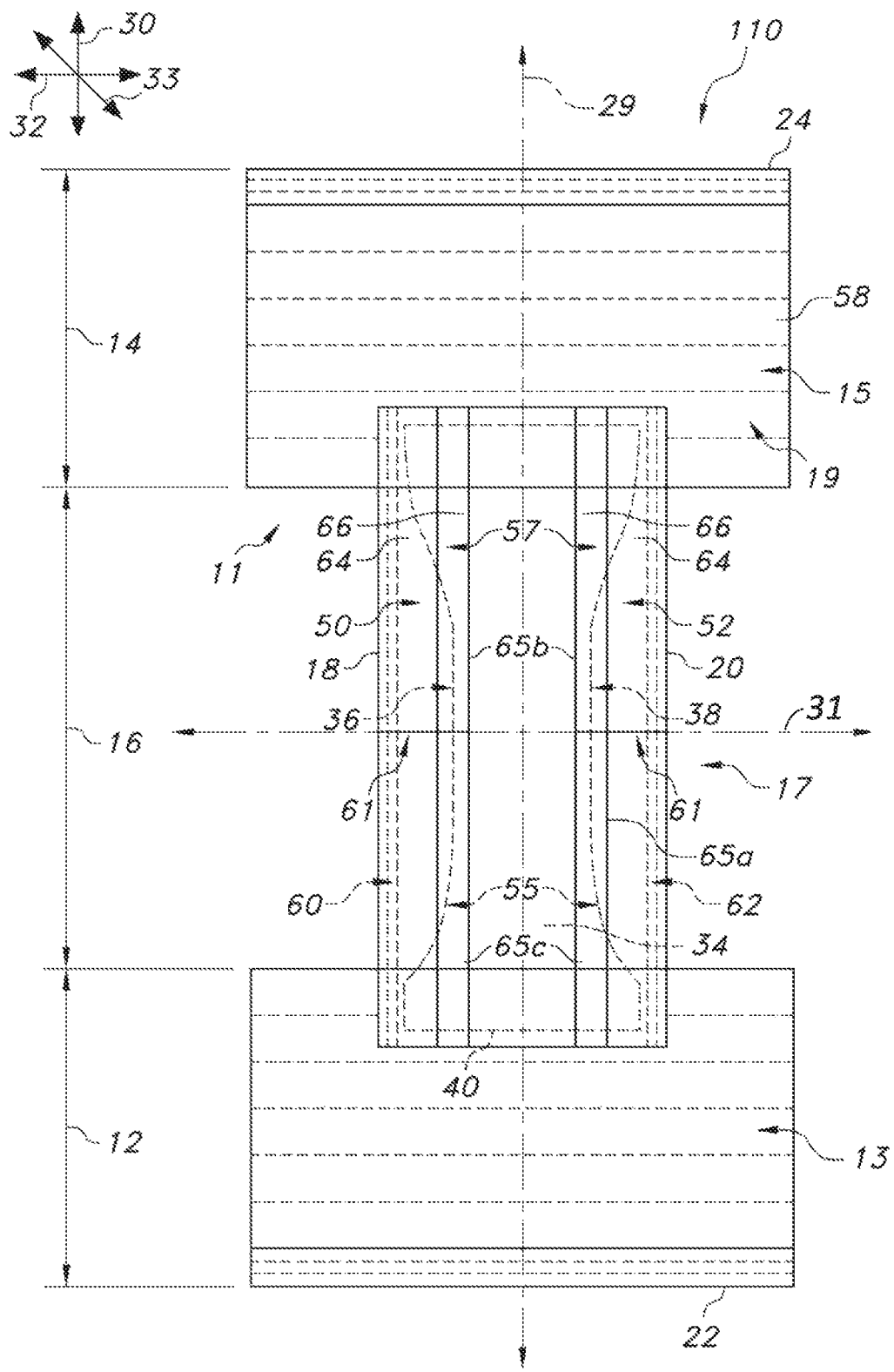
FIG. 2A is a top plan view of the absorbent article of FIG. 1A in a stretched, laid flat and unfastened condition.

Referring to FIGS. 1-7, a non-limiting illustration of an absorbent article 10 for example, a diaper, is illustrated. Other embodiments of the absorbent article 10 can include, but are not limited to, training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure. For example, the absorbent article 110 in FIGS. 1A and 2A provides an exemplary embodiment of an absorbent article 110 that can be manufactured in cross-direction manufacturing process.

The absorbent article 10 illustrated in FIGS. 1 through 7 can include a chassis 11. The absorbent article 10 can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. In the embodiment depicted in FIGS. 1A and 2A, a three-piece construction of an absorbent article 110 is depicted where the absorbent article 110 can have a chassis 11 including a front waist panel 13 defining the front waist region 12, a rear waist panel 15 defining the rear waist region 14, and an absorbent panel 17 defining the crotch region 16 of the absorbent article 110. The absorbent panel 17 can extend between the front waist panel 13 and the rear waist panel 15. In some embodiments, the absorbent panel 17 can overlap the front waist panel 13 and the rear waist panel 15. The absorbent panel 17 can be bonded to the front waist panel 13 and the rear waist panel 15 to define a three-piece construction. However, it is contemplated that an absorbent article can be manufactured in a cross-direction without being a three-piece construction garment which is also sometimes referred to as a one-piece construction (not shown) as the front waist panel 13 and the rear waist panel 15 are integral with one another by way of commonly connected components forming the waist panel such as a bodyside liner and/or an outer cover which can envelope the absorbent panel 17 or simply cover the garment side of the absorbent panel 17.

The absorbent article 10, 110 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent article 10 illustrated in FIG. 2. In other embodiments, the longitudinal side edges 18, 20 can be curved between the front waist edge 22 and the rear waist edge 24. In the absorbent article 110 of FIGS. 1A and 2A, the longitudinal side edges 18, 20 can include portions of the front waist panel 13, the absorbent panel 17, and the rear waist panel 15.

The front waist region 12 can include the portion of the absorbent article 10, 110 that, when worn, is positioned at least in part on the front of the wearer while the rear waist region 14 can include the portion of the absorbent article 10, 110 that, when worn, is positioned at least in part on the back of the wearer. The crotch region 16 of the absorbent article 10, 110 can include the portion of the absorbent article 10, 110 that, when worn, is positioned between the legs of the wearer and can partially cover the lower torso of the wearer. Dimensionally, the front waist region 12 can be defined as the front one-third of the overall longitudinal dimension of the absorbent article 10 measuring from the front waist edge 22 to the rear waist edge 24. The rear waist region can be defined as the rear one-third of the longitudinal dimension of the absorbent article 10 and the crotch region 16 is the middle one-third of the longitudinal dimension of the overall absorbent article 10. The waist edges, 22 and 24, of the absorbent article 10, 110 are configured to encircle the waist of the wearer and together define a central waist opening 23 (as labeled in FIG. 1 and FIG. 1A) for the waist of the wearer. Portions of the longitudinal side edges 18, 20 in the crotch region 16 can generally define leg openings for the legs of the wearer when the absorbent article 10, 110 is worn.

Figure 3:
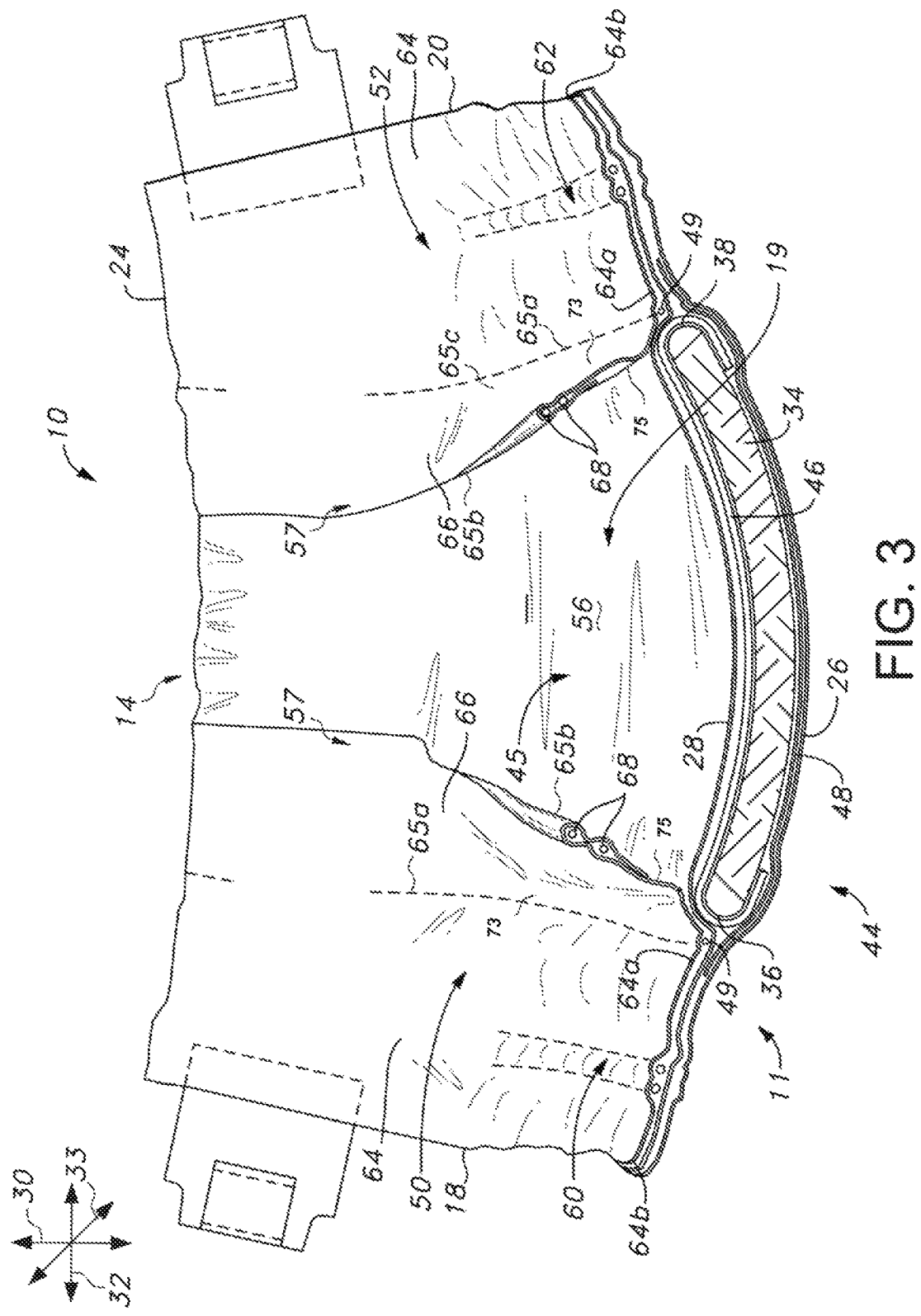
FIG. 3 is a cross-section of the absorbent article of FIG. 2 taken along line 3-3.

The absorbent article 10, 110 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated embodiment, can coincide with the length and width of the absorbent article 10. As illustrated in FIGS. 2 and 2A, the absorbent article 10, 110 can have a longitudinal axis 29 extending in the longitudinal direction 30, and a lateral axis 31 extending in the lateral direction 32. The lateral axis 31 is located midway between the front waist edge 22 and the rear waist edge 24. As shown in FIG. 3, the absorbent article 10 also has a vertical or z-direction axis 100 extending in the vertical direction 33.

Figure 4:
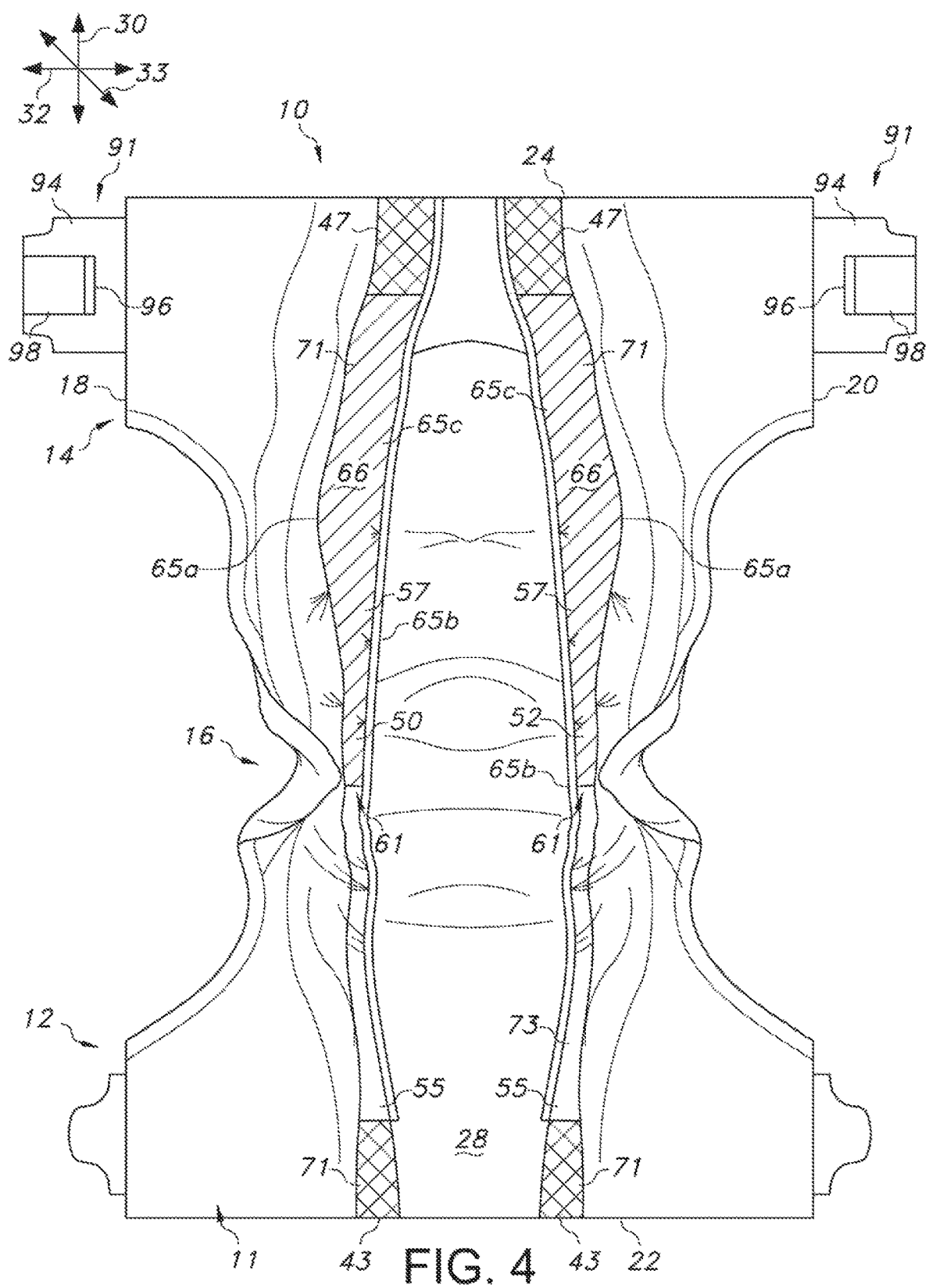
FIG. 4 is a perspective view of the absorbent article of FIG. 2 in a relaxed state showing the BM containment flaps in an upstanding configuration.

The chassis 11 can include an absorbent body 34. The absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10, 110. The absorbent body 34 can have a first end edge 40 that is opposite a second end edge 42, respectively, which, in an embodiment, can form portions of the waist edges, 22 and 24, respectively, of the absorbent article 10. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent article 10, 110. The bodyside liner 28, the outer cover 26, and the absorbent body 34 can form part of an absorbent assembly 44. In the absorbent article 110 of FIGS. 1A and 2A, the absorbent panel 17 can form the absorbent assembly 44. The absorbent assembly 44 can also include a fluid transfer layer 46 (as shown in FIG. 4) and a fluid acquisition layer (not shown) between the bodyside liner 28 and the fluid transfer layer 46 as is known in the art. The absorbent assembly 44 can also include a spacer layer 48 (as shown in FIG. 3) disposed between the absorbent body 34 and the outer cover 26.

The absorbent article 10, 110 can be configured to contain and/or absorb liquid, solid, and semi-solid body exudates discharged from the wearer. To this end, the absorbent article 10, 110 is fitted with a pair of containment flaps 50, 52 which are configured to provide a barrier to the lateral flow of body exudates. To further enhance containment and/or absorption of body exudates, the absorbent article 10, 110 can optionally include a waist containment member (not shown) which form pockets to further retain body exudates. See, for example, PCT/US15/23620, filed 31 Mar. 2015; PCT/US15/23596, filed 31 Mar. 2015; PCT/US15/23637, filed 31 Mar. 2015; PCT/US15/38271, filed 29 Jun. 2015; PCT/US15/47672, filed 31 Aug. 2015; and 62/212,051, filed 31 Aug. 2015 each of which is incorporated herein by reference in its entirety. In some embodiments, the waist containment member can be disposed in the rear waist region 14 of the absorbent article 10, 110. Such a waist containment member can be additionally or alternatively disposed in the front waist region 12 of the absorbent article 10, 110 or in an intermediate portion of the absorbent article 10, 110 (not shown).

The absorbent article 10, 110 can further include leg elastic members 60, 62 as are known to those skilled in the art. The leg elastic members 60, 62 can be attached to the outer cover 26 and/or the bodyside liner 28 along the opposite longitudinal side edges, 18 and 20, and positioned in the crotch region 16 of the absorbent article 10, 110. The leg elastic members 60, 62 can be parallel to the longitudinal axis 29 as shown in FIGS. 2 and 2A or can be curved as is known in the art. The leg elastic members 60, 62 can provide elasticized leg cuffs.

Additional details regarding each of these elements of the absorbent article 10, 110 described herein can be found below and with reference to the FIGS. 1-7.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10, 110. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A. G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the bodyside liner 28 can be constructed as described herein and it also may be apertured to enhance evaporation of urine in the event the inner layer is vapor permeable.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent article 10, 110 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10, 110 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent article 10, 110. The absorbent body 34 can have a length and width that can be less than or equal to the length and width of the absorbent article 10, 110.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material or in an alternate embodiment be comprised entirely of superabsorbent material.

If a spacer layer 48 is present, the absorbent body 34 can be disposed on the spacer layer 48 and superposed over the outer cover 26. The spacer layer 48 can be bonded to the outer cover 26, for example, by adhesive. In some embodiments, a spacer layer 48 may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer 46 and/or a spacer layer 48, can be positioned between the absorbent body 34 and the outer cover 26, such as illustrated in FIG. 4. The absorbent body 34 can be bonded to the fluid transfer layer 46 and/or the spacer layer 48. Typically the absorbent body 34 will be completely enveloped by a core wrap material such as a tissue wrap or a nonwoven material such a meltblown web, a spunbond web or both.

Bodyside Liner:

The bodyside liner 28 of the absorbent article 10, 110 can overlay the absorbent body 34 and the outer cover 26 and can isolate the wearer's skin from liquid waste retained by the absorbent body 34. In various embodiments, a fluid transfer layer 46 can be positioned between the bodyside liner 28 and the absorbent body 34. In various embodiments, an acquisition layer (not shown) can be positioned between the bodyside liner 28 and the absorbent body 34 or a fluid transfer layer 46, if present. In various embodiments, the bodyside liner 28 can be bonded to the acquisition layer, or to the fluid transfer layer 46 if no acquisition layer is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer 46, if present, and/or an acquisition layer, if present, and/or a spacer layer 48, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. It is contemplated that the bodyside liner 28 may be narrower than the outer cover 26. However, in other embodiments, the bodyside liner 28 and the outer cover 26 may be of the same dimensions in width and length, for example, as depicted in the embodiments illustrated in FIG. 1. In other embodiments, the bodyside liner 28 can be of greater width than the outer cover 26. It is also contemplated that the bodyside liner 28 may not extend beyond the absorbent body 34 and/or may not be secured to the outer cover 26. In some embodiments, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material such as a central region of material which is different from one or both of the lateral regions of the bodyside liner 28 (not shown). The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Pat. No. 9,327,473 to Kirby et al.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10, 110. In other aspects, the bodyside liner 28 can be stretchable, and more suitably elastic, in both the lateral and the longitudinal directions 32, 30, respectively.

Containment Flaps:

In an embodiment, the absorbent article 10, 110 can include a pair of containment flaps 50, 52. Examples of containment flaps can be found in U.S. Pat. No. 9,259,362 granted 16 Feb. 2016 Robert L. Popp et al. and U.S. Pat. No. 9,168,181 granted 27 Oct. 2015 Robert L. Popp et al. each of which is incorporated herein by reference in its entirety.

The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent article 10, 110 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10, through the crotch region 16 to the rear waist region 14 of the absorbent article 10. In some embodiments, the containment flaps 50, 52 can extend in a direction substantially parallel to the longitudinal axis 29 of the absorbent article 10, however, in other embodiments, the containment flaps 50, 52 can be curved, as is known in the art. In other embodiments, such as the absorbent article 110 in FIGS. 1A and 2A, the containment flaps 50, 52 can be disposed on the absorbent panel 17 in the crotch region 16.

In embodiments where the containment flaps 50, 52 are coupled to the chassis 11, the containment flaps 50, 52 can be bonded to the bodyside liner 28 with a barrier adhesive 49, as shown in FIG. 3 or the containment flaps 50, 52 can be bonded to the outer cover 26 with a barrier adhesive 49 in some embodiments where the bodyside liner 28 does not extend the full lateral width of the outer cover 26. Of course, the containment flaps 50, 52 can be bonded to other components of the chassis 11 and can be bonded with other suitable means other than a barrier adhesive 49 or with several areas or beads of barrier adhesive. In addition to adhesive, other bonding means can be employed including, but not limited to, pressure bonding and ultrasonic bonding. The containment flaps 50, 52 can be constructed of a fibrous material which can be similar to the material forming the bodyside liner 28, including, but not limited to a spunbond-meltblown-spunbond ("SMS") material. Other conventional materials, including, but not limited to, polymer films, can also be employed. In addition, laminates of materials including multiple layers of film and/or nonwovens can be used to form the containment flap material.

The containment flaps 50, 52 in an embodiment such as is shown in FIGS. 1-7 can each include a base portion 64 and a projection portion 66. The base portion 64 and the projection portion 66 can be formed from the same materials or from different materials. In an embodiment, the containment flaps 50, 52 can comprise only the projection portion 66 with the projection portion 66 defining the entire containment flap 50, 52. In such situations, the base portion 64 may be eliminated or it may be formed from one of the other components such as an extension of the bodyside liner 28, the outer cover 26 or from a separate and distinct piece of material (not shown).

The base portion 64 can be bonded to the chassis 11, for example, to the bodyside liner 28 or the outer cover 26 or another component of the chassis 11. The base portion 64 can include an interior end 64a and an exterior end 64b. The projection portion 66 can be separated from the base portion 64 at the interior end 64a of the base portion 64. As used in this context, the projection portion 66 is separated from the base portion 64 at the interior end 64a of the base portion 64 in that the interior end 64a of the base portion 64 defines a transition between the projection portion 66 and the base portion 64. The interior end 64a of the base portion 64 can be located near and/or utilize all or a portion of the barrier adhesive 49 or a separate barrier adhesive 49 or other attachment means. In some embodiments, the exterior ends 64b of the base portion 64 of the containment flaps 50, 52 can laterally extend to the respective longitudinal side edges 18, 20 of the absorbent article 10. In other embodiments, the exterior ends 64b of the base portion 64 can end laterally inward of the respective longitudinal side edges 18, 20 of the absorbent article 10, 110. The containment flaps 50, 52 also each include a projection portion 66 that is configured to extend away from the body facing surface 19 of the chassis 11 at least in the crotch region 16 when the absorbent article 10 is in a relaxed configuration, as illustrated in FIGS. 3 and 4. The containment flaps 50, 52 can include a tack-down region 71 in either or both of the front waist region 12 and the rear waist region 14 where the projection portion 66 is coupled to the body facing surface 19 of the chassis 11. See FIG. 2.

In a more simplified version, the base portion 64 of the containment flaps 50, 52 can be eliminated (not shown) or can be made from a separate piece of material such that the projection portion 66 forms the entire containment flap 50, 52. In this case, the containment flaps 50, 52 can be regarded as having a proximal edge 65a and a distal edge 65b joined by a medial section 65c. See in particular, FIGS. 3, 4, 4A and 4B. The proximal edge 65a can be attached to the chassis 11 including direct or indirect attachment to any of the components including the bodyside liner 28, the outer cover 26 or any of the other components of the absorbent article 10. Thus, the barrier adhesive 49 can be used to attach the proximal edge 65a to the chassis 11 and this barrier adhesive 49 can be the same as or separate from the barrier adhesive used to attach the interior end 64a of the base portion 64 to the chassis 11.

It is contemplated that the containment flaps 50, 52 can be of various configurations and shapes, and can be constructed by various methods. For example, the containment flaps 50, 52 of FIG. 2 depict a vertical containment flap 50, 52 with a tack-down region 71 in both the front and rear waist regions 12, 14 where the projection portion 66 of each containment flap 50, 52 is tacked down to the bodyside liner 28 towards or away from the longitudinal axis 29 of the absorbent article 10. However, the containment flaps 50, 52 can include a tack-down region 71 where the projection portion 66 of each of the containment flaps 50, 52 is folded back upon itself and coupled to itself and the bodyside liner 28 in a "C-shape" configuration, as described in U.S. Pat. No. 5,895,382 to Robert L. Popp et al. As yet another alternative, it is contemplated that the containment flaps 50, 52 can be constructed in a "T-shape" configuration, such as described in U.S. Pat. No. 9,259,362 by Robert L. Popp et al. Such a configuration can also include a tack-down region 71 in either or both of the front and rear waist regions 12, 14, respectively. Of course, other configurations of containment flaps 50, 52 can be used in the absorbent article 10, 110 and still remain within the scope of this disclosure.

The containment flaps 50, 52 can include one or more flap elastic members 68, such as the two flap elastic strands depicted in FIGS. 2 and 3. Of course, while two elastic members 68 are shown in each containment flap 50, 52, it is contemplated that the containment flaps 50, 52 can be configured with one or three or more elastic members 68. As shown in the Figures, the elastic members 68 are located adjacent the flap distal edges 65b but they can also be located in any other portion of the containment flaps including adjacent the flap proximal portion 65a and the flap medial portion 65c.

Suitable elastic materials for the flap elastic members 68 can include, but are not limited to, spandex elastomeric strands, sheets, strands, or ribbons of natural or synthetic rubber, thermoplastic elastomeric materials, or heat activated elastomeric materials. The elastic members 68 can be any elastomeric material capable of being elongated at least about 50 percent, desirably about 350 percent, and capable of recovering to within at least about 250 percent, and desirably about 150 percent of its original length after being elongated about 300 percent. The elastic members 68 can be a spandex elastomeric strand(s) such as, for example, a LYCRA thread commercially available from E. I. DuPont de Nemours and Co. Alternatively, the elastic members 68 can be composed of a thermoplastic elastomer or a natural or a synthetic rubber commercially available from J.P.S. Elastomerics Corp. Alternatively, the elastic members 68 can also be composed of a heat activated elastic material such as PEBAX, commercially available from Atochem, Inc., which can be activated with heat treatment after the elastic members 68d are secured to the containment flaps 50, 52.

Alternatively or additionally, the containment flaps 50, 52 can be composed of a material exhibiting elastic properties itself thereby eliminating the need for the use of separate flap elastic members 68. In an alternate embodiment, the containment flaps 50, 52, and in particular the projection portions 66, can be formed from an elastic material or laminate such as a stretch film laminate as described herein which optionally can be supplemented with flap elastics adjacent the distal edges 65b, alternately adjacent the proximal edges 65a, alternately adjacent the medial section 65c/41 or a combination of any or all of the foregoing regions of the projection portions 66 forming the containment flaps 50, 52. Example suitable materials that may be used as containment flaps 50, 52 include vertical film laminate materials, stretch film laminate materials, or elastic laminate structures. One specific example material is the elastic film laminate material called SABBEEL herein, which is described in U.S. Pat. No. 8,287,677, titled "Printable Elastic Composite" and is expressly incorporated herein in its entirety. Additionally, it should be understood that these are only example materials. More generally, any material having at least some of the below described properties are contemplated by this disclosure for use as containment flaps 50, 52.

The flap elastic members 68, as illustrated in FIGS. 2 and 3, can have two strands of elastomeric material extending longitudinally in the projection portion 66 of the containment flaps 50, 52, in generally parallel, spaced relation with each other. The elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 45 of the absorbent assembly 44 in a generally upright orientation of the containment flaps 50, 52, especially in the crotch region 16 of the absorbent article 10, when the absorbent article 10 is in a relaxed configuration.

During manufacture of the containment flaps 50, 52 at least a portion of the elastic members 68 can be bonded to the containment flaps 50, 52 while the elastic members 68 are elongated. The percent elongation of the elastic members 68 can be, for example, about 110% to about 350%. The elastic members 68 can be coated with adhesive while elongated to a specified length prior to attaching the elastic members 68 to the containment flaps 50, 52. In a stretched condition, the length of the elastic members 68 which have adhesive coupled thereto can provide an active flap elastic region 70 in the containment flaps 50, 52, as labeled in FIG. 2, which will gather upon relaxation of the absorbent article 10. The active flap elastic region 70 of containment flaps 50, 52 can be of a longitudinal length that is less than the length of the absorbent article 10, 110. In this exemplary method of bonding the elastic members 68 to the containment flaps 50, 52, the portion of the elastic members 68 not coated with adhesive will retract after the elastic members 68 and the absorbent article 10 are cut in manufacturing to form an individual absorbent article 10. As noted above, the relaxing of the elastic members 68 in the active flap elastic region 70 when the absorbent article 10, 110 is in a relaxed condition can cause each containment flap 50, 52 to gather and cause the projection portion 66 of each containment flap 50, 52 to extend away from the body facing surface 19 of the chassis 11 (e.g., the body facing surface 45 of the absorbent assembly 44 or the body facing surface 56 of the bodyside liner 28), as depicted in FIGS. 2 and 3.

Of course, the elastic members 68 can be bonded to the containment flaps 50, 52 in various other ways as known by those of skill in the art to provide an active flap elastic region 70, which is within the scope of this disclosure. Additionally, the active flap elastic regions 70 can be shorter or longer than depicted herein, including extending to the front waist edge 22 and the rear waist edge 24, and still be within the scope of this disclosure.

Figure 4A:
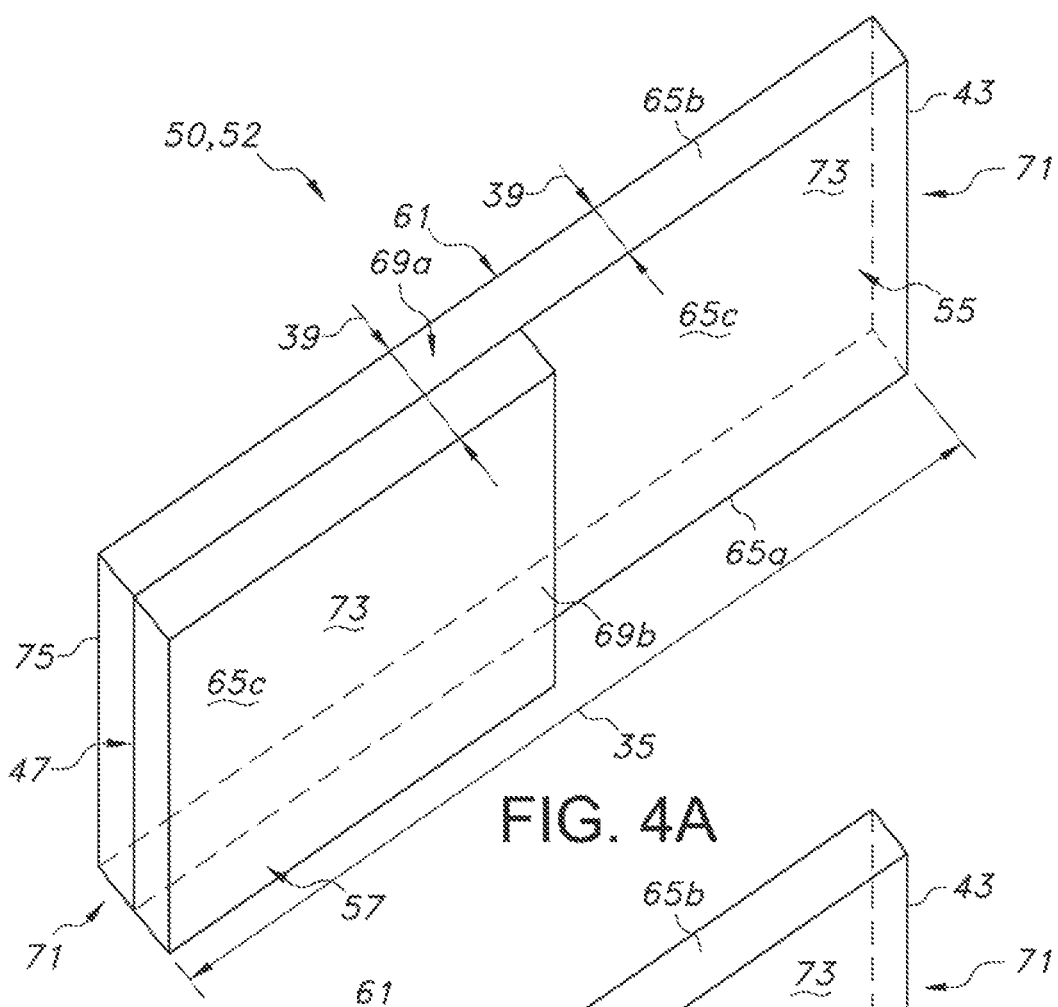
FIG. 4A is a perspective side view of a BM containment flap according to the present invention with a first portion adjacent the front waist portion of the article and a second portion adjacent the rear waist portion of the product.
Figure 4B:
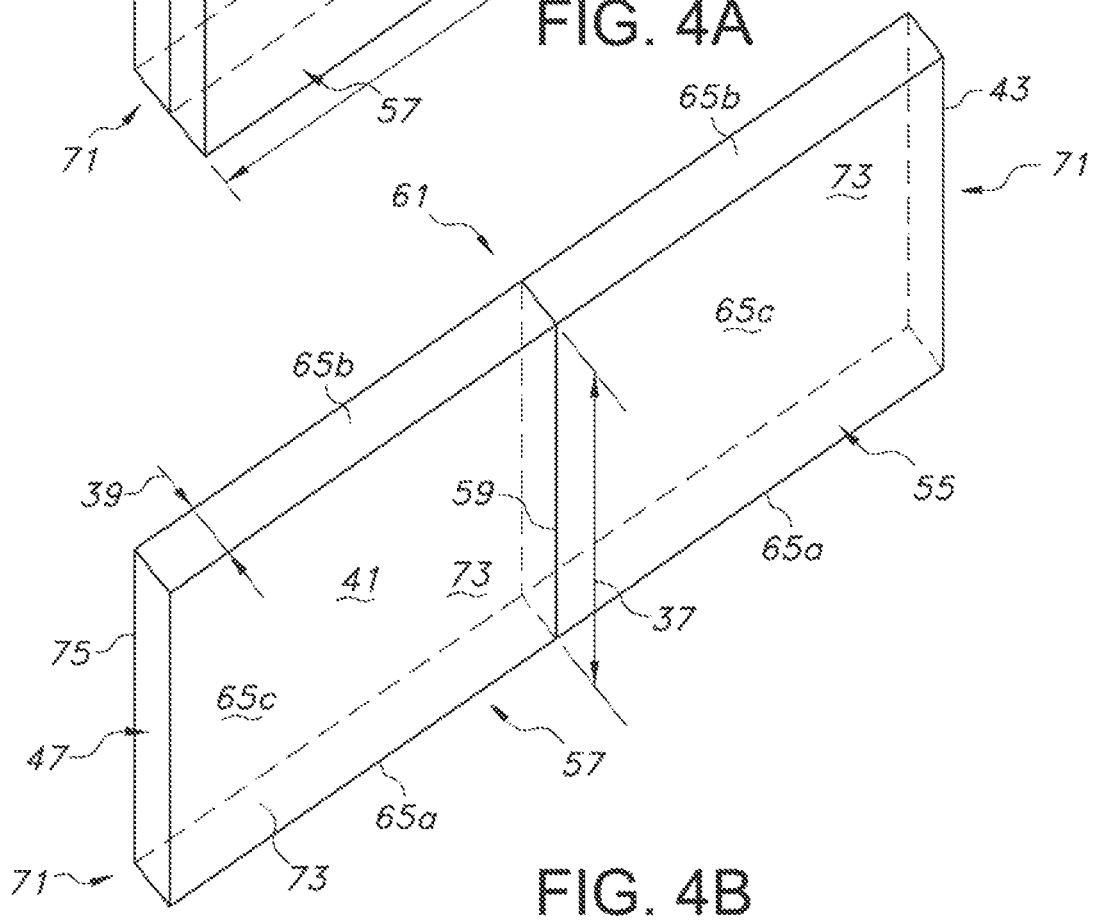
FIG. 4B is a perspective side view of another BM containment flap according to the present invention with a first portion adjacent the front waist portion of the article and a second portion adjacent the rear waist portion of the product.

Turing to FIGS. 1-7 and in particular FIGS. 4A and 4B, each of the containment flaps 50, 52 has a first end 43 located in the front waist region 12 and a second end 47 located in the rear waist region 14. As a result, each of the containment flaps 50, 52 defines a length 35 as measured between the first end 43 and the second end 47 of each containment flap 50, 52 when the article 10 is in a stretched, laid flat configuration such as is shown in FIGS. 2 and 2A. Each of the containment flaps 50, 52 has a flap body facing surface 73 and a flap absorbent facing surface 75 defining a thickness 39 therebetween. Each of the containment flaps 50, 52 defines a height 37 as measured between the proximal edge 65a and the distal edge 65b of each containment flap when the article 10 is in a stretched, laid flat configuration such as is shown in FIGS. 2 and 2A.

Each of the containment flaps has a first portion 55 located primarily in the front end region in the front waist region 12 and a second portion 57 located primarily in the rear end region in the rear waist region 14. The first portion 55 is joined directly or indirectly to the second portion 57 at a flap juncture 61. See FIGS. 2, 2A, 4A and 4B. The first portion 55 can extend in the longitudinal direction 30 from the front waist region 14 into the crotch region 16. In the same fashion, the second portion 57 can extend in the longitudinal direction 30 from the rear waist region 14 into the crotch region 16. The flap juncture 61 is located in the crotch region 16 and runs generally parallel to the lateral axis 31. Alternatively, the flap juncture 61 can be at an angle to the later axis 31. In an embodiment, the flap juncture 61 is located at or in the vicinity of the lateral axis 31 which is located midway between the front waist edge 22 and the rear waist edge 24. In an embodiment, the flap juncture 61 is located within 3 centimeters of the lateral axis 31, alternatively within 2 centimeters of the lateral axis, alternatively within 1 centimeter of the lateral axis. If the lateral axis 31 also corresponds with the lateral fold line of the absorbent article 10 when the article is packed for shipping, it is desirable that the flap juncture 61 be in alignment with the fold line (not shown) or rearward of the lateral axis 31 and/or the fold line (not shown) so as to remain in the rear end section. The lateral axis 31 can be regarded as dividing the absorbent article 10 into the front end section which includes the front waist region 12 and a portion of the crotch region 16 and the rear end section which includes the rear waist region 14 and a portion of the crotch region 16.

It has been found that it is desirable that the second portion 57 and the flap juncture 61 not extend past the lateral fold line of the article 10 into the front end region, or not extend into the front region very far. For example, the second portion 57 and the flap juncture 61 may extend past the lateral fold line of the article 10 into the front end region as much as one inch (2.54 mm). As described, one of the properties that the second portion 57 of the containment flaps 50, 52 can have is a higher bending stiffness as compared to the front portion 55. Thus, if this stiffer material contains a crease due to the absorbent article 10 being folded, the folding of the material can create an undesirable curve in the material that can interfere with the formation of a good seal between the flap body facing surface 73 and the buttocks of the wearer. However, it has been found that the second portion 57 and the flap juncture 61 may extend past the lateral fold line of the article 10 into the front end region up to 2.54 mm without interfering with improved function of flaps 50, 52.

One of the desired results of an absorbent article 10 according to the present invention is to form a tighter seal between the flap body facing surface 73 of the second portion 57 of the containment flaps 50, 52 and in particular the projection portion 66 of the containment flaps 50, 52 and the skin in the buttocks region of the wearer. As a result, it has been found that the second portion 57 of the second portion 57 of the containment flaps 50, 52 should have one or more properties that are different than the properties of the front portion 55 of the second portion 57 of the containment flaps 50, 52. One of the properties is the bending stiffness of the material forming the containment flaps 50, 52. A stiffer material in the rear end section has been found to provide a better seal against the intrusion of BMs and in particular pasty BMs between the flap body facing surface 73 of the second portion 57 of the containment flaps 50, 52 and the skin of the wearer. Conversely, it has been found that using this stiffer material in the front end region is not desirable for several reasons. First, this stiffer material can cause undue skin irritation in the genital area of the wearer thereby making the article 10 more uncomfortable to wear. Second, as mentioned above, if this stiffer material extends into the front end region, the folding of the article 10 for packaging and shipping can cause a somewhat permanent set which in turn can form a convex "U" that tends to sit off the skin of the wearer for a certain amount of time after donning. If, during this period, a BM occurs, this convex portion of the flap 50, 52 can create an area with little or no seal with the skin of the wearer thereby providing a channel for leakage of the BM towards the longitudinal side edges 18, 20 of the article 10.

The stiffness and/or other properties of the second portion 57 as opposed to the first portion 55 of the containment flaps 50, 52 can be imparted in a number of ways. As shown in FIG. 4A, the overall containment flap 50, 52 can be made from one piece of material 69a such as any material commonly used to form BM containment flaps. Then a second piece of material 69b can be bonded or otherwise attached to one surface of the containment flap 50, 52. As shown in FIG. 4A, this second piece of material 69b is located on the flap body facing surface 73 but it also may be placed on the flap absorbent facing surface 75 or on both surfaces. It may be joined by any known means such as adhesives, thermal bonding, ultrasonic bonding and the like as well as combinations of such means or other means of attachment. The second piece of material 69b may be attached to the first piece of material 69a of the containment flap 50, 52 in a tensioned or non-tensioned state and/or the containment flap 50, 52 may also be in a tensioned or non-tensioned state when attaching the second piece of material 69b to the first piece of material 69a.

As shown in FIG. 4B, the first portion 55 and the second portion 57 are different materials which are joined to one another at the flap juncture 61. The flap juncture 61 can be formed in the same way as described with respect to FIG. 4A such as adhesives, thermal bonding, ultrasonic bonding and the like as well as combinations of such means or other means of attachment. The flap juncture 61 can be, for example, in the form of a butt seam, an overlapping seam, a "Y" seam where the end of one piece of material is spit to form a "Y" and the open ends of the "Y" straddle and are joined to either side of the end of the other piece of material. Other forms of joinder can also be used. As shown in FIG. 4B the flap juncture 61 is a relatively straight line but it can also take on other forms such as a curved line or a slanted line relative to the lateral axis 31.

Any number of techniques can be used to make the second portion 57 more stiff than the first portion 55. Different basis weights or materials may be used, more layers of materials may be used, different types of materials may be used and higher levels of adhesive, preferably internally between layers may be used to increase the stiffness. A non-elastic material may be layered with an elastic material to provide the desired material properties. Still other techniques include using bond patterns to provide the desired level of stiffness. For instance, a relatively higher concentration of bonds may be used. Where specific directional stiffness is desired, a line pattern of bonds may be used to impart the desired directional stiffness. For example, a line bond extending along the height of one of the containment flaps 50, 52 between about 50% to about 80% of the height of the flap may provide the desired level of stiffness in the direction of the flap height (e.g. generally in the product lateral-direction 32). In addition, when additional layers of material are being used, they may extend the entire length 35 and height 37 of the second portion 57 or only a portion thereof. Still further, the second portion 57 may have more strands of elastics 68 than the front portion 55.

One method of measuring stiffness of the containment flaps in the lateral direction (between the proximal edge 65a and the distal edge 65b) of the containment flaps 50, 52, generally in the direction of the lateral axis 31, is the Gurley Stiffness test method which measures the stiffness in milligrams (mg). It is desirable that the second portion 57 of the containment flaps 50, 52 have a Gurley stiffness of from about 80 mg to about 190 mg, alternatively from about 100 mg to about 160 mg, and alternatively from about 120 mg to about 140 mg. Additionally, it is desirable that the second portion 57 have a Gurley stiffness that is about 15 times to about 30 times greater than the Gurley stiffness of the first portion 55, alternatively, about 18 times to about 27 times greater than the Gurley stiffness of the first portion 55, alternatively, about 20 to about 25 times greater than the Gurley stiffness of the first portion 55.

Generally, the containment flaps 50, 52 will have a flap height that ranges from about 30 millimeters (mm) to about 60 mm, alternatively from about 35 mm to about 50 mm, alternatively from about 38 mm to about 45 mm. Dimensionally, the second portion 57 may have a higher height 37 than the front portion 55. The average height of the second portion 57 can range from about 5 to about 100 percent higher than the average height of the first portion 55, alternatively from about 10 to about 50 percent higher than the average height of the first portion 57, alternatively from about 10 to about 30 percent higher than the average height of the first portion 57. The average height of the first portion 55 is based upon the height 37 of the first portion 55 from the proximal edge 65a to the distal edge 65b as measured from the flap first end 43 (discounting the tack down region 71) to the flap juncture 61 and the average height of the second portion 57 is based upon the height 37 of the second portion 57 from the proximal edge 65a to the distal edge 65b as measured from the flap second end 47 (discounting the tack down region 71) to the flap juncture 61. As an example, if the flap first portion 55 had an average height of 20 mm, a 5 percent average higher height in the second portion would equal 1.05×20=21 mm and a 100 percent average higher height in the second portion would equal 2.0×20=40 mm. While the distal edge 65b of the second portion 57 is shown generally parallel to the proximal edge 65a in the Figures, it is also possible for the distal edge 65b to be non-parallel to the proximal edge 65a. For example, the height of the second portion 57 may increase from the flap juncture 61 to the second end 47. It also may increase and then decrease as it approaches the second end 47. Other variations in the flap height 37 are also contemplated to be within the scope of the present disclosure. The same variability may also be present in the first portion 55 of the containment flaps 50, 52.

As noted in the preceding paragraph, the average height is taken over the distance from either the flap first end 43 or the flap second end 47 to the flap juncture 61 (discounting the tack down region 71). It is within the scope of the present disclosure for there to be a third portion (not shown) of material intermediate and joining the first portion 55 and the second portion 57 at which point the flap juncture 61 would be considered a line on the containment flap 50, 52 parallel to the lateral axis 31.

In addition to the flap height 37 varying between the second portion 57 and the first portion 55, the thickness 39 of the second portion 57 may vary as compared to the first portion 55. Here again, the thickness 39 should be an average thickness 39 of the material forming the second portion 57 as compared to the first portion 55. In this regard, it is desirable that the average thickness 39 of the second portion 57 be greater than the average thickness 39 of the first portion 55. Generally, the containment flaps 50, 52 will have an average flap thickness 39 that ranges from about 0.30 millimeters (mm) to about 0.90 mm for the first portion 55 and from about 1.50 mm to about 2.2 mm for the second portion 57, alternatively from about 0.4 mm to about 0.8 mm for the first portion 55 and from about 1.70 mm to about 2.0 mm for the second portion 57, alternatively from about 0.45 mm to about 0.7 mm for the first portion 55 and from about 1.75 mm to about 1.95 mm for the second portion 57. Measurements for calculating the thickness should be done under a load of 0.05 pounds per square inch (psi) (345 pascals (Pa)) and at least three measurements per portion. If the average of any three measurements in the second portion 57 is greater than the average of any three measurements in the first portion 55, then average thickness of the second portion 57 is deemed to be greater than the average thickness of the first portion 55.

The basis weight of the second portion 57 can be greater than the basis weight of the first portion 55. This can be due to the material forming the second portion 57 in single layer form having a higher basis weight than the first portion 55 or because the second portion 57 is formed of multiple layers or more layers than the first portion 55. Generally, the containment flaps 50, 52 will have a flap basis weight that ranges from about 40 grams per square meter (gsm) to about 60 gsm for the first portion 55 and from about 170 gsm to about 270 gsm for the second portion 57, alternatively from about 45 gsm to about 55 gsm for the first portion 55 and from about 190 gsm to about 250 gsm for the second portion 57, alternatively from about 47 gsm to about 53 gsm for the first portion 55 and from about 210 gsm to about 230 gsm for the second portion 57. In determining the basis weight, all the components of the first portion 55 or second portion 57 should be taken into account from the proximal edge 65a to the distal edge 65b as well as the medial section 41 and any elastic members 68.

In addition to the properties of stiffness, height, thickness and basis weight, the elasticity and tensional forces of the second portion 57 may be different, and desirably more elastic than the first portion 55. Here again, this may be accomplished in a number of ways such as by using greater numbers of elastic members 68, elastic members 68 which are larger in size as in having a greater decitex value than the elastic members 68 in the first portion 55, or different configurations such as ribbons of elastic as opposed to more circular strands. Still further, the degree of elasticity and tensional force can be varied by varying the amount of tension the elastics are put under prior to attachment to the other materials forming the containment flaps 50, 52. Another way to increase the elasticity and elongation and tension forces in the second portion 57 as compared to the first portion 55 is to attach another layer or layers of elastic material such as the above-described stretch film laminate material to one or both of the flap body facing surface 73 and flap absorbent facing surface 75 of the containment flaps 50, 52. In some embodiments, the increased elastic properties extend all along the flap height 37 in the second portion 57, for instance from the apex of the flap to the base of the flap. For instance, elastic strands may be added running longitudinally along the flaps 50, 52 along the entire height of the flaps. Alternatively, a material applied to the flaps 50, 52 may have elastic properties and it may cover the entire height 37 of the flaps 50, 52. However, in other embodiments, the increased elastic properties may extend along only a portion of the flap height. As some examples, the increased elastic properties may extend only along between about 30% to about 90% of the flap height 37, alternatively about 40% to about 80%, or alternatively about 50% to about 70% of the flap height 37, beginning at the distal edge 65b and extending toward proximal edge 65a.

As to the property of elasticity and tensional force, one particularly suitable material is the aforementioned stretch film laminate. One suitable version is a three layer laminate comprising an interior layer of apertured elastomeric film (which can be breathable or non-breathable and optionally apertured) laminated to two layers of fibrous nonwoven web material. Typically in these types of materials the elastomeric film is pre-stretched during the laminate formation. In some cases, the material may be formed off-line and then applied to flaps 50, 51. However, in other embodiments the laminate may be formed during an on-line process. This material is particularly desirable because it can provide multiple differences in properties in that it can be used to vary one or more of the stiffness, the thickness, the height, the basis weight, the coefficient of friction and the elasticity of the second portion 57 as compared to the first portion 55. Example suitable elastomeric films, including stretch film laminates, are commercially available from companies including 3M Co., Clopay Co., and Tredegar Co from their personal hygiene grade material lines.

The degree of tensional forces in the second portion 57 as compared to the first portion 55 can be express in grams force. The test method for calculating the grams force tension or elongation force in samples of each of the first 55 and second 57 portions of the containment flaps 50, 52 is set forth in the below test procedures. Generally it is desirable that the second portion 57 have an elongation force at 50% strain of from about 240 grams force to about 375 grams force, alternatively from about 275 grams force to about 350 grams force, alternatively from about 320 grams force to about 340 grams force. Additionally, it is desirable that the second portion 57 have an elongation force that is about 2 times to about 5 times greater than the elongation force of the first portion 55, alternatively, about 2.5 times to about 4.5 times greater than the elongation force of the first portion 55, alternatively, about 3 times to about 4 times greater than the elongation force of the first portion 55.

Another desirable property of the second portion 57 is the surface roughness of the flap body facing surface 73 of the second portion 57 as compared to the flap body facing surface 73 of the first portion 55. This can be expressed by the coefficient of friction as determined by the Kawabata Surface Friction test as described in the below test procedures. When placed on a wearer, the containment flaps 50, 52 will be under tension. As the wearer moves around, this tension may act to drag the elastics over the wearer's buttocks. However, if the flaps 50, 52 have great enough surface roughness, as determined by the Kawabata Surface Friction test, the flaps 50, 52 may resist this dragging force and remain on in place the wearer's buttocks. Accordingly, material may be chosen to be placed in the second portion 57 that has a greater surface roughness than the standard flap material of the first portion 55. Therefore, it is generally desirable that the flap body facing surface 73 of the second portion 57 have a coefficient of friction that is higher than the front portion 55 thereby indicating that the body facing surface 73 of the second portion 57 is rougher than the first portion 55. Generally it is desirable that the flap body facing surface 73 have a coefficient of friction value (MIU) of from about 0.60 MIU to about 0.90 MIU and a mean deviation of MIU (MMD) from about 0.020 (MMD) to about 0.040 (MMD), alternatively from about 0.70 MIU to about 0.9 MIU and a mean deviation of MIU (MMD) from about 0.020 (MMD) to about 0.030 (MMD), and alternatively from about 0.80 MIU to about 0.9 MIU and a mean deviation of MIU (MMD) from about 0.020 (MMD) to about 0.025 (MMD). In addition, this value should be from about 0 percent to about 75 percent higher than the value for the flap body facing surface 73 of the first portion 55, alternatively from about 10 percent to about 75 percent higher than the value for the flap body facing surface 73 of the second portion 57 of the first portion 55, alternatively from about 15 percent to about 75 percent higher than the value for the flap body facing surface 73 of the first portion 55, and alternatively from about 15 percent to about 35 percent higher than the value for the flap body facing surface 73 of the first portion 55.

The alteration in the properties of the second portion 57 of the containment flaps 50, 52 as compared to the first portion 55 can be visually and texturally conveyed to the wearer and other people associated with the use of the absorbent article by varying the visual distinctiveness of the second portion 57 as compared to the first portion 55. One way to do this is by altering the coloring or shading of the second portion 57 as compared to the first portion 55. For example, the overall containment flap 50, 52 can be made a conventional white color but all or a portion of the second portion 57 of the containment flap 50, 52 can be made to be a different color such as purple, blue, green, pink or another color. Alternatively, just the flap body facing surface 73 can be made a different color or shade of color as compared to the remainder of the second portion 57 of the containment flap 50, 52 or as compared to the remainder of the second portion 57 and the first portion 55 of the containment flap 50, 52. By "visually distinct" it is meant that at least one property of the second portion 57 of the containment flaps 50, 52 is observable by a person with natural or corrected 20/20 vision while holding the absorbent article 10 at an arm's length distance from the viewer's eyes.

In addition to making all or a portion of the second portion visually distinct by differences in color or shading, printed indicia or patterns of printing may be used in the same manner as the color and color shading described above. Still further, bonding and/or embossing patterns may be used to change the appearance of all or a portion of the second portion 57 as compared to the first portion 55. Lastly, any combination of the foregoing methods of altering the visual appearance and textural feel of the second portion 57 from the first portion 55 may be used in association with the present disclosure.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10, 110. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the base portion 64 of each containment flap 50, 52 and the bodyside liner 28 as depicted in FIGS. 2, 2A and 3, between the base portion 64 of each containment flap 50, 52 and the outer cover 26, or between the bodyside liner 28 and the outer cover 26. The leg elastic members 60, 62 can be one or more elastic components near each longitudinal side edge 18, 20. For example, the leg elastic members 60, 62 as illustrated herein each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10, 110 without departing from the scope of this disclosure.

Fastening System:

In an embodiment, the absorbent article 10, can include a fastening system. The fastening system can include one or more back fasteners 91 and one or more front fasteners 92. The embodiments being shown in FIGS. 1 and 2 depict embodiments with one front fastener 92. Portions of the fastening system may be included in the front waist region 12, rear waist region 14, or both.

The fastening system can be configured to secure the absorbent article 10 about the waist of the wearer in a fastened condition as shown in FIG. 1 and help maintain the absorbent article 10 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIG. 2.

Containment Flap Attributes

Figure 5:
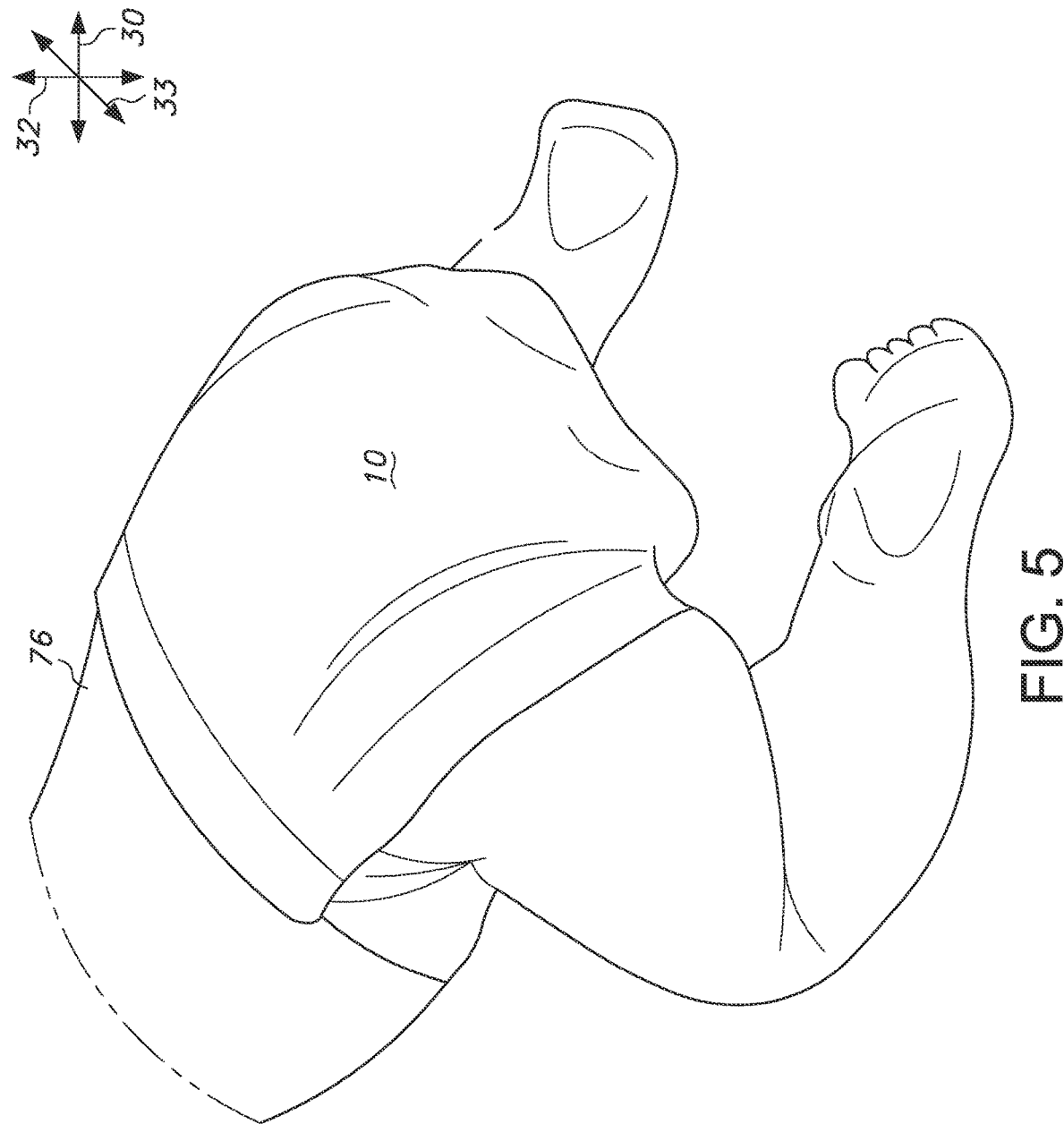
FIG. 5 is a perspective view of an absorbent article according to the present invention fitted to a torso representing a child from the rear in a partially bent over (from the waist) configuration.

The effectiveness of the present design can be further understood and illustrated with reference to FIGS. 5, 6, 6A, 7, 8, 9 and 10 of the drawings. FIG. 5 is a perspective view of a partial torso of a wearer, in this case a small infant, in a bent over and kneeling condition wearing and absorbent article 10 according to the present invention. FIG. 6 is a partially cutaway perspective view of the buttocks area of the wearer with sufficient components of the article 10 removed to show the BM containment flaps 50, 52 in contact with the torso so as to be able to see the portions of the containment flaps 50, 52 which would form the flap body facing surface 73 of both the first portion 55 and the second portion 57 of the containment flaps 50, 52.

FIG. 6A is a partial perspective view of an absorbent article 10 according to the present invention being worn and positioned against the buttocks 76 of the wearer during the voiding of a pasty BM 77. The purpose of this drawing is to illustrate what was observed during loading of absorbent articles 10 when fitted to a mannequin torso. Due to the improved tighter fitting of the second portion 57 to the skin of the buttocks of the wearer, a much more effective skin to flap seal 78 was formed from the distal edge 65b, across the medial section 65c to the proximal edge 65a of the second portion 57 of the containment flaps 50, 52 and the skin of the wearer. As a result, there was a much more effective containment of the pasty BM within the void space created between the flap absorbent facing surface 75 and the body facing surface 56 of the bodyside liner 28.

The effectiveness of this seal 78 between the second portion 57 of the containment flaps 50, 52 and the skin of the wearer is illustrated in FIG. 7 which is intended to shown the stain pattern left on the skin and buttocks by the pasty BM 77 when the absorbent article 10 is completely removed. As can be seen from FIG. 7, there is a relatively clean demarcation line 79 between soiled and unsoiled areas on the wearer's skin. This relatively small exposed area of the wearer to the BM, in contrast to the relatively higher exposed area shown in FIG. 10, illustrates the benefit of the containment flaps 50, 52 of the present disclosure in promoting good skin health by controlling the flow of the BM under the flaps where it is trapped away from the skin of the wearer.

In contrast, FIG. 8 is meant to show a conventional absorbent article design 10, again a diaper, in a stretched, flat and unfastened condition with conventional BM containment flaps 50, 52 that do not have a first portion 55 and a second portion 57 with different properties. FIG. 9 is a view similar to that of the absorbent article 10 according to the present invention shown in FIG. 6 and FIG. 10 is a view similar to that of the absorbent article 10 according to the present invention shown in FIG. 7. The purpose of FIG. 10 of the drawings is to illustrate what was observed during loading of conventional absorbent articles 10 when fitted to a mannequin torso. Due to the lack of the improved second portion 57 adjacent the skin of the buttocks of the wearer, a much more looser skin to flap seal 78 was formed from the distal edge 65b, across the medial section 65c to the proximal edge 65a of the second portion 57 of the containment flaps 50, 52 and the skin of the wearer. As a result, significant portions of the excreted pasty BM was able to leak between the distal edge 65b of the conventional absorbent article 10 and the skin of the wearer or to push or drag the distal edge 65b outward resulting in a much wider area of soiling of the skin of the buttocks as can been seen by the representative wider stain area in FIG. 10. This is to be contrasted with much more effective containment of the pasty BM within the void space created between the flap absorbent facing surface 75 and the body facing surface 56 of the bodyside liner 28 as shown in FIG. 7.

This higher degree of containment of the BM by the present invention results in many advantages to the wearer and caregiver. First, with less skin of the wearer exposed to the voided BM, there is less skin subject to the common side effects associate with wearing soiled absorbent articles such as diaper rash and other skin disorders. This in turn results in greater comfort for the wearer. Second, with less skin exposed to the voided BM, there is less skin area that requires cleaning with the soiled absorbent article is removed. This in turn saves time and results in the use of less cleaning supplies such as moist wipes and other cleaning materials. Third, with a tighter seal against the skin, due to the fact that there is no or less leakage between the flap facing surface 73 and the skin of the wearer, there is a lower risk of side leakage out the lateral side edges 18, 20 of the absorbent article 10.

Turning to FIG. 11, there is shown an absorbent article 10 in a similar view to that of FIGS. 6 and 9, the difference being that the containment flaps 50, 52 are made entirely of the second portion 57 design in both the first portion 55 and second portion 57. Testing with this configuration indicated that the distal edges 65b of both the containment flaps 50 and 52 would both unduly move towards the longitudinal centerline or axis 29. This resulted in at least two negative attributes. First, if the containment flaps 50, 52 were made of stiffer material, they tended to pinch and restrict the perennial area of the wearer. This was particular troublesome when the absorbent article 10 was being worn by a male wearer as it would tend to impinge upon the male genitalia. Secondly, because the containment flaps 50, 52 moved more closely to the longitudinal axis 29, the distal edges 65b of the containment flaps 50, 52 unduly impinged the anus of the wearer. This could result in situations where the voided BM would either be blocked by the containment flaps 50, 52 or, the voided BM would be deposited on the flap body facing surface 73 before it had a chance to enter the void space created between the flap absorbent facing surface 75 of the containment flaps 50, 52 and the body facing surface 56 of the bodyside liner 28. This in turn could cause the voided BM to be forced towards the longitudinal side edges 18, 20 of the absorbent article 10 resulting in leakage out the sides of the absorbent article 10 and soiling of the wearer's clothing and/or surrounding environment. As a result, it can be seen that second portion 57 should be restricted to the rear portion of the absorbent article 10.

Test Procedures
Kawabata Surface Friction Test

The surface friction and thus the softness and ability to form a tight seal against the skin of the wearer of the second portion 57 of the containment flaps 50, 52 as compared to the first portion 55 can be determined in a variety of different ways. One test method is the Kawabata surface friction test which demonstrates differences in the surface softness of the containment flap materials by measuring the coefficient of friction (MIU). In particular, the lower the MIU value, the smoother/softer the surface and this in turn results in greater skin contact with the buttocks of the wearer and a better seal against leakage of pasty BMs. It has been found that creating the second portion 57 of the containment flaps 50, 52 with smoother and flatter surfaces, increases the overall sealing effect of the flap material against the skin of the wearer.

The Kawabata surface friction test uses a Kawabata Evaluation System (KES-SE) surface friction electronic instrument manufactured by Kato Tech Company, Japan which is equipped with a calculation circuit to measure the frictional coefficient (MIU) and the mean deviation of the coefficient of friction (MMD) of the materials used to form the flap body facing surfaces 73 of the first and second portions 55, 57 of the containment flaps 50, 52.

During the test, a specimen is placed on a sliding table at a specified speed. The moving direction and distance are detected by a potentiometer as the displacement output voltage. Surface friction is measured by a roughness sensor positioned against the specimen surface (the flap body facing surface 73), or by using a frictional force sensor with weight. The frictional force sensor is connected to a frictional force transducer with a linear differential transformer. The measured values are closely related to the hand touch feeling of a material's surface. In particular, a KES Surface Friction and Surface Roughness Electronic Unit (ICES-SE-U) is used, together with a KES Surface Friction and Surface Roughness Mechanical Unit (KES-SE-U) which includes a 50-gram sensor weight, and a specimen fixation weight. The testing laboratory has a conditioned testing environment of 23+−0.2 degree C. and 50+−0.5% relative humidity. The probe for measuring friction is a silicone probe from Kato Tech Company. The required number of specimens is cut from a sample. For instance, one specimen is cut from each of the front portion 55 and the back portion 57 of each of flap 50 and flap 52. In other examples, multiple specimens, such as two or three, may be cut from each of the front portion 55 and the back portion 57 of each flap 50 and 52. In these examples, the measured property values from each of the specimens may be averaged to determine an overall value for the front portion 55 and the back portion 57. The samples may be taken at a location beginning between approximately 7.6 cm and 8.9 cm from the front waist edge or rear waist edge. Each specimen is cut to a dimension of approximately 1 inch by 1 inch (approximately 2.54 centimeters (cm) by 2.54 cm), or the specimens may be cut to have a size that is 2.54 cm by the height 37 of the flap 50, 52, for instance where the flap is cut from the article at proximal edge 65a and cut to be 2.54 cm long. The samples are tested with the surface testing being performed only in the machine direction, e.g. along the longitudinal direction of the sample as it would have been oriented within the article. The sample is mounted such that the machine direction is parallel to the moving direction of the bed. The measured distance on the sample is 2 cm.

The test is run according to the following steps:
1. The cable labeled FR on the mechanical unit is connected to the FR-DT port located in back of the KES unit.
2. The analog meter for surface friction is positioned on the left side of the electronic unit and is labeled FRICTION. The zero adjust dial for surface friction testing is labeled FR-ZERO.
3. Press the black button labeled FR-T.
4. Turn the CHECK OSC/BAL/MES knob to OSC. The needle of each analog meter should be positioned at approximately 10 volts. If the deviation is larger than 2 volts, do not use the equipment; repair is required.
5. Position the FRIC DT/GU knob to DT.
6. Toggle the SENS switch to the appropriate position; e.g., the H position for this test.
7. Turn the CHECK OSC/BAL/MES knob to BAL. The needle on the analog meter labeled FRICTION should be positioned at 0+−0.1 volt. When it is necessary to adjust the BAL, use a small screwdriver and adjust the FR-BAL and FRC-BAL in the following order: first adjust the FR-BAL, and then adjust the FRC-BAL.
8. Turn the CHECK OSC/BAL/MES knob to MES. The digital readout should display+−00.00 volt. If it is necessary to adjust the MES, unlock the zero adjust dial labeled FR-ZERO, make the necessary adjustment, and relock the dial.
9. Turn the SPEED knob to 1 mm/s to set the testing speed.
10. Remove the screws to the specimen fixing chuck and remove the specimen fixing chuck from the specimen table.
11. While holding the white knob of the frictional force detector housing, loosen the fixing screw and adjust the sensor hanging shaft height so the center of the frictional force sensor hanging shaft is approximately aligned horizontally with the top of the specimen table. Once approximately aligned, tighten the fixing screw.
12. Place the specimen fixing chuck on the specimen table. Place the screws in the specimen fixing chuck, and tighten sufficiently so the specimen fixing chuck remains in place.
13. Select the KES program by double-clicking the KES TEST Ver 6.36 icon.
14. Select Tester (S) from the menu bar at the top of the KES-FB System Measurement Program screen.
15. Select SE and Friction Measure from the drop-down menu.
16. Friction Sensitivity: When H is selected on the electronic unit, select H as a standard setting, as in this test.
17. Speed: Select 1 and 1 speed setting.
18. Friction Static Load: Select 50 as a standard input value when using the sensor weight, as was used in this test.
19. Loosen the screws on the specimen fixing chuck sufficiently that the specimen can be positioned under the chuck. Lift the top of the fixing chuck; place the specimen on the specimen table and under the chuck so that it is approximately centered on the specimen table. Tighten the specimen fixing chuck screws sufficiently to hold the specimen firmly in place. Avoid touching the test areas.
20. Place the specimen fixation weight over the specimen, so the narrow side of the specimen fixation weight is approximately centered between the specimen fixing chuck screws and aligned approximately 1 cm from the right edge of the specimen thing chuck.
21. Ensure the digital display reads+−00.00 volt. If it does not, unlock the zero adjust dial labeled FR-ZERO, make the necessary adjustment, and relock the dial.
22. Carefully place the frictional force sensor onto the sensor hanging shaft.
23. Ensure the frictional force sensor is properly seated on the hanging shaft by placing a finger lightly on the frictional force sensor's free end. When the frictional force sensor is properly seated, ensure the digital readout displays+−00.00 volt. If necessary, carefully reposition the frictional force sensor.
24. Select WARP for the MD testing.
25. Select Measure (M) from the menu bar at the top of the screen.
26. Select Manual Start from the drop-down menu.
27. Press the black button labeled SR-T.
28. Press the black button labeled FR-T.
29. Press the black button labeled MIU.
30. Click OK or press either the Enter key or spacebar.
31. Electronic unit: Press and hold for approximately 1 second the green button labeled MES START. The specimen table on the mechanical unit will begin to move. A graph will display as the test runs. At the completion of the test, the results will display.
32. Record the coefficient of friction (MIU1) in the forward direction (INT) to the nearest 0.01 unit.
33. Record the mean deviation of the coefficient of friction (MMD1) the forward direction (INT) to the nearest 0.01 unit.
34. Record the static load in grams.
35. Record the speed in mm/second.
36. Record the sensitivity as H.
37. Report the coefficient of friction value (MIU1) to the nearest 0.001 unit by multiplying by the appropriate factor. For the load set at 50 g, speed at 1 mm/s and sensitivity=H, the factor for MIU is 0.1 and the factor for MMD is 0.01.
38. Report the mean deviation of MIU (MMD1) to the nearest 0.0001 unit by multiplying by the appropriate factor.

Elongation Test

The Elongation Test is a one cycle elongation test used to measure the elongation characteristics of an absorbent article, and more particularly of a test specimen comprising a containment flap sample cut from the respective first 55 and second 57 portions of each of the left and right containment flaps 50, 52. In particular, the Test may be used to determine the degree or amount of tensional forces in grams force exhibited by the materials forming the front 55 and rear 57 portions of the containment flaps 50, 52. As is supported by the test data below, the rear portion 57 has the ability to exert more tensional force which in turn means less sagging and leaking when the absorbent article 10 is being worn and used. The Test measures load values of a test sample placed under a particular amount of strain (e.g., elongated to a particular elongation). In this Test, the strain was set at 50%. Such load values are determined during the elongation phase of the Test for the single cycle. The Test is conducted on the front 55 and rear 57 portions of the containment flaps and the results are compared.

Sample Preparation

Ten samples of the test specimen should be subjected to the Elongation Test. Each sample should be approximately 1 inch (2.54 cm) long by and have a width equal to the flap height 37. Data was gathered for 10 samples of 4 separate test specimens representing a portion of the front flap portion 55 of the left containment flap 50, a portion of the rear flap portion 57 of the left containment flap 50, a portion of the front flap portion 55 of the right containment flap 52, and a portion of the rear flap portion 57 of the right containment flap 52.

Each of the samples of the specimens should be unattached from any article or portion of an article they were previously attached to, such as leg or waist elastic structures, impermeable outer covers or liners (if not manufactured to be secured to the absorbent composite), etc., at least in the region to be used as a sample.

Where the containment flaps 50, 52 were attached to a manufactured absorbent article, the flaps may be unattached by breaking any bonds between the containment flaps 50, 52 and the absorbent article. This may involve applying a solvent to the bond area to dissolve the bonds. Alternatively, the containment flaps 50, 52 may be torn away from the absorbent article along the bond juncture, or a knife may be used to cut the containment flaps 50, 52 free from the absorbent article just above where the containment flaps 50, 52 are bonded to the article.

The samples from the front portion 55 of the flaps 50, 52 used for testing should be taken beginning approximately 8 cm from the front waist edge and extending in the longitudinal direction 30 toward the rear waist edge to have a length of approximately 2.54 cm. The width, or height, of these samples will then be equal to the flap height 37 after the flaps 50, 52 have been detached from the article. Conversely, the samples from the rear portion 57 of the flaps 50, 52 used for testing should be taken beginning approximately 9 cm from the rear waist edge and extending in the longitudinal direction 30 toward the front waist edge to have a length of approximately 2.54 cm. As with the samples from the front portions 55, the samples from the rear portions 57 will have a width, or height, dimension equal to the flap height 37. Again, ten samples of each of the four specimens were tested according the tests described below.

Test Apparatus and Materials

The following test apparatus and materials are used to conduct the Elongation Test.

1) Constant Rate of Extension (CRE) tensile tester: MTS tensile tester criterion model 43, available from MTS Systems Corporation, Research Triangle Park, N.C., USA.

2) Load cells: A suitable cell selected so that the majority of the peak load values fall between the manufacturer's recommended ranges of the load cell's full scale value. Load cell Model 100N available from MTS Systems Corporation is preferred.

3) Operating software and data acquisition system: MTS TESTWORKS for Windows software version 4.12, available from MTS® Systems Corporation.

4) Grips: pneumatic-action grips, top and bottom, identified as part number 2712-003 available from Instron Corporation, Canton, Mass. USA.

5) Grip faces: 25 mm by 76 mm.

Test Conditions

Reasonable ambient conditions should be used for sample testing, such as 73+/−2 degrees Fahrenheit (about 23 degrees Celsius) and a relative humidity of 50+/−2 percent. If the samples are stored under substantially different conditions, the samples should be measured after they equilibrate to laboratory conditions, which takes approximately 4 hours.

The instruments used should be calibrated as described in the manufacturer's instructions for each instrument.

The tensile tester conditions are as follows:
Data acquisition rate: 100 Hz
Test speed: 508 mm/min, extension and retraction.
Full scale load: 10,000 grams-force
Gage length: 1 inch (2.54 cm)
Number of cycles: 1
Test End Point: 50% strain.

Test Procedure

Calibrate the load cell using the TESTWORKS software at the beginning of each work session. Using the tensile frame pushbutton controls for cross-head position, move the grips to provide a gage length (distance between grips) of 1 inch (2.54 cm). Calibrate the software to this initial gage length. Place the sample to be tested lengthwise so that it is centered between the grips, held in a centered position within each grip, and oriented correctly (e.g., with the widthwise dimension running transverse to the length between the grips), e.g., with the vertical (e.g., side) edges of the sample perpendicular to the grip faces. Close the grips on the sample, holding the sample in such a way as to minimize slack in the sample without placing the sample under tension.

Ensure that the load at this point is between 10 and 15 grams-force. If the load is greater than 15 grams-force, release the lower grip and zero the load cell. Re-close the lower grip, again ensuring that the sample is neither under tension nor buckled with excessive slack. Continue checking the starting load and following the above procedure until the starting load is within the desired range, which is between 10 and 15 grams-force in this case.

Run the three cycle test using the above parameters by clicking on the RUN button. When the test is complete, save the data to a sample file. Remove the sample from the grips. Run the above procedures for the remaining samples of a given specimen. The data for all samples should be saved to a single file.

Report the data for each sample as follows: Load @ 40% strain—extension to the nearest 0.01 grams-force.

Gurley Stiffness Test

A Gurley Stiffness Test is commonly used to determine the stiffness of a test specimen (in this case the first portion 55 and the second portion 57 of the containment flaps 50, 52 and in particular the projection portion 66 of the containment flaps 50, 52) with respect to a bending moment produced by a force that is directed perpendicular to the plane substantially defined by the length and width of the specimen being tested. A description of a Gurley Stiffness Test is set forth in TAPPI Standard Test T543 om-94 (Bending Resistance of Paper (Gurley type tester)). One suitable testing apparatus for conducting the Gurley Stiffness Test is a Gurley Digital Stiffness Tester, Model 31644 manufactured by Teledyne Gurley, a business having offices in Troy, N.Y. For purposes of the present disclosure, the stated Gurley stiffness values are reported in terms of milligrams (mg) of force.

In general, the Gurley Digital Stiffness Tester consists of a pendulum with slots for attaching various weights. The specimen to be tested presses the pendulum to the right and to the left resulting in two readings. The readings are positively correlated with a specimen's stiffness. The two readings are then averaged and multiplied by a factor. This factor is determined by the specimen size, the distance from the center pivot, and the weight used on the pendulum. Methodology of the Gurley Stiffness Test is set forth below.

For purposes of the present disclosure, test specimens are prepared, e.g., taken from a larger sample or product, by cutting the specimen to have its length in the longitudinal or machine direction of the product. As an example, for the present disclosure where the containment flaps 50, 52 are being tested, the specimens are cut from the diaper to include the proximal edge 65a (just above the point of attachment to the chassis 11), the medial portion 65c and the distal edge 65b. For this test, each specimen should be approximately 2.54 cm long and instead of having a width, or height, that is equal to the flap height 37, should have a width that is also 2.54 cm. For example, each specimen should be cut to have a width of 2.54 cm if the flap height 37 is greater than 2.54 cm. Testing was performed to determine stiffness in both the longitudinal direction of each specimen, e.g. along the length of each specimen, and in the lateral direction, e.g. along the height of each specimen. Each sample was selected from portions of the articles as described with respect to the Elongation Test.

To conduct the Gurley Stiffness Test using the Gurley Digital Stiffness Tester, the base of the instrument is first leveled by adjusting the leveling screw until the level's bubble is centered and the pendulum's pointer indicates zero. After turning the power on, the specimen is used to determine the appropriate weight and the weight position on the pendulum to obtain a reading between 2 and 6 on the scale/display. The switches are set to correspond to the weight being used, the weight's position on the pendulum, the width of the specimen being tested, and the length of the specimen.

For each specimen, the specimen strip is centered over the pendulum such that 6.4 mm+−1 mm (or 0.25 inches+−0.04 inches) overlaps the top of the pendulum and 6.4 mm+−1 mm (or 0.25 inches+−0.04 inches) is held in the jaws of the Tester. The system is reset so that the display reads 00-000-00. The Motor-Direction switch is operated to engage the clamp arm to press the specimen against the pendulum. Both a left reading and a right reading are taken, and an average reading is determined. The SELECT button on the Tester is then pressed to obtain the stiffness (in milligrams) calculation and the stiffness is recorded. The aforementioned steps are repeated for each test specimen in the sample group.

Basis Weight

Basis weights for ten samples for each of 4 specimens representing a portion of the front flap portion 55 of the left containment flap 50, a portion of the rear flap portion 57 of the left containment flap 50, a portion of the front flap portion 55 of the right containment flap 52, and a portion of the rear flap portion 57 of the right containment flap 52 were also gathered.

In order to measure the basis weights for each of the samples, the samples were prepared to have a length and width of approximately 2.54 cm. The samples were removed from a manufactured article as described previously, and cut to the proper dimensions. Each sample was selected from portions of the articles as described with respect to the Elongation Test.

Each sample was then weighed in grams, and the area of each sample, in conjunction with the measured weight, was used to generate a gsm value for each sample.

Thickness

The thickness for ten samples for each of 4 specimens representing a portion of the front flap portion 55 of the left containment flap 50, a portion of the rear flap portion 57 of the left containment flap 50, a portion of the front flap portion 55 of the right containment flap 52, and a portion of the rear flap portion 57 of the right containment flap 52 were also gathered.

In order to measure the thicknesses for each of the samples, the samples were prepared to have a length and width of approximately 2.54 cm. The samples were removed from a manufactured article as described previously, and cut to the proper dimensions. Each sample was selected from portions of the articles as described with respect to the Elongation Test.

A Mitutoyo thickness gauge was used to measure the thicknesses of each of the samples. The Mitutoyo is a platen-based thickness gauge and was loaded at 0.05 psi (0.35 kPa), and a brass platen was used. The measured thicknesses of each portion of the example diapers are recorded in the below listed tables.

EXAMPLES

To illustrate the improved handling of BM, two separate absorbent article configurations (Diaper 1 and Diaper 2) were made. In both configurations, the design was a diaper. A common chassis was formed similar to that shown in FIGS. 1 through 7. Both samples were conventional diaper designs with the exception of the containment flaps 50, 52. The diapers were premium tier diapers acquired commercially from Kimberly-Clark Co.

The containment flaps 50, 52 for both Diaper 1 and Diaper 2 was of a configuration such as is shown in FIG. 4A. The first piece of flap material 69a was a 10 gsm-17 gsm SMS which was used to form both the base portion 64 and the projection portion 66 of the containment flaps 50, 52. The first piece of flap material 69a ran from the front waist edge 22 to the rear waist edge 24 and had an overall flap length 35 of 40 mm when the diaper chassis 11 was in a stretched, laid flat and unattached condition such as is shown in FIG. 2. The Diapers included base portion 64 which had a lateral width of between 1 mm-3 mm and was adhesively attached to the chassis 11 from its exterior end 64b to its interior end 64a. The projection portion 66 had a proximal edge 65a coextensive with the interior end 64a, a distal edge 65b and a medial portion 65c. Adjacent and adhesively encased within the distal edge 65b were two strands of LYCRA thread. The elastic members 68 were attached to the first piece of flap material equidistant from the front waist edge 22 and the rear waist edge 24. Each of the flap projection portions 66 had a tack down region 71 at either end of the diaper chassis 11.

The Diapers also included an elasticized waist panel having a width in the lateral direction 32 and a length of 60 mm in the longitudinal direction attached to the body facing surface of the bodyside liner 56 and to the base portion 64 and projection portion 66 of the containment flaps 50, 52 outside the active flap elastic region 70 in the rear waist region 14.

Both Diaper 1 and Diaper 2 had a second piece of flap material 69b attached to the flap body facing surface 73 to form the flap second portion 57. In an unattached, relaxed state, each of the second pieces of flap material 73 had a length dimension in the longitudinal direction 30 and a width dimension in the lateral direction 32 equal to the flap height 37 before attachment to the flap body facing surface 73 of each of the containment flaps 50, 52. The combination of the first piece of flap material 69a and the second piece of flap material 69b formed the second portion 57 of the containment flaps 50, 52. The second portion 57 did not extend past the lateral axis 31 of the article 10.

Diaper 1 utilized the aforementioned stretch film laminate composite as the second piece of flap material 69b and Diaper 2 utilized the aforementioned Tredegar elastic material. Each of the materials was pre-stretched between about 30% and about 60% before attachment to the flaps 50, 52, and were attached using standard flap adhesive.

The containment flaps for each of the samples (Samples 1 and 2) were evaluated for Kawabata surface friction, Elongation, Gurley stiffness, basis weight and thickness for both the first portion 55 and the second portion 57 of both the left and right containment flaps 50, 52 for each of the samples. The results are set forth in Tables 1 through 5 below.

TABLE 1

| Sample # | Diaper 1 - First Portion Basis Weight (gsm) | | | Diaper 1 - Second Portion Basis Weight (gsm) | | |
|---|---|---|---|---|---|---|
| | Left Flap | Right Flap | Left/Right Average | Left Flap | Right Flap | Left/Right Average |
| 1 | 46.50 | 49.45 | 47.97 | 254.98 | 240.10 | 247.54 |
| 2 | 41.54 | 47.90 | 44.72 | 249.86 | 234.36 | 242.11 |
| 3 | 43.56 | 44.02 | 43.79 | 237.77 | 229.56 | 233.66 |
| 4 | 45.73 | 41.70 | 43.71 | 274.04 | 259.01 | 266.52 |
| 5 | 53.94 | 46.50 | 50.22 | 230.49 | 230.02 | 230.25 |
| 6 | 49.29 | 49.91 | 49.60 | 245.83 | 276.21 | 261.02 |
| 7 | 45.11 | 44.18 | 44.64 | 269.08 | 216.54 | 242.81 |
| 8 | 45.26 | 45.26 | 45.26 | 243.97 | 232.97 | 238.47 |
| 9 | 46.04 | 44.02 | 45.03 | 273.42 | 254.98 | 264.20 |
| 10 | 49.76 | 48.52 | 49.14 | 250.02 | 245.83 | 247.92 |
| Total Average | 46.67 | 46.14 | 46.41 | 252.94 | 241.96 | 247.45 |

| Sample # | Diaper 2 - First Portion Basis Weight (gsm) | | | Diaper 2 - Second Portion Basis Weight (gsm) | | |
|---|---|---|---|---|---|---|
| | Left Flap | Right Flap | Left/Right Average | Left Flap | Right Flap | Left/Right Average |
| 1 | 49.45 | 50.84 | 50.14 | 225.53 | 262.26 | 243.89 |
| 2 | 52.39 | 50.07 | 51.23 | 212.82 | 212.20 | 212.51 |
| 3 | 49.91 | 52.39 | 51.15 | 212.35 | 201.97 | 207.16 |
| 4 | 55.80 | 48.98 | 52.39 | 207.24 | 202.12 | 204.68 |
| 5 | 49.91 | 53.94 | 51.93 | 199.80 | 211.27 | 205.53 |
| 6 | 51.77 | 51.93 | 51.85 | 220.72 | 277.92 | 249.32 |
| 7 | 50.69 | 52.39 | 51.54 | 198.87 | 212.04 | 205.45 |
| 8 | 52.55 | 56.89 | 54.72 | 240.10 | 277.92 | 259.01 |
| 9 | 45.57 | 52.08 | 48.83 | 224.91 | 217.78 | 221.34 |
| 10 | 48.83 | 53.94 | 51.38 | 194.68 | 216.38 | 205.53 |
| Total Average | 50.69 | 52.34 | 51.51 | 213.70 | 229.18 | 221.44 |

TABLE 2

| Sample # | Diaper 1 - First Portion Thickness (mm) | | | Diaper 1 - Second Portion Thickness (mm) | | |
|---|---|---|---|---|---|---|
| | Left Flap | Right Flap | Left/Right Average | Left Flap | Right Flap | Left/Right Average |
| 1 | 0.740 | 0.600 | 0.670 | 2.690 | 2.085 | 2.388 |
| 2 | 0.783 | 0.778 | 0.781 | 2.503 | 1.968 | 2.236 |
| 3 | 0.754 | 0.642 | 0.698 | 2.335 | 2.260 | 2.298 |
| 4 | 0.670 | 0.881 | 0.776 | 2.395 | 2.301 | 2.348 |
| 5 | 0.754 | 0.525 | 0.640 | 2.125 | 2.329 | 2.227 |
| 6 | 0.753 | 0.794 | 0.774 | 2.498 | 2.331 | 2.415 |
| 7 | 0.848 | 0.612 | 0.730 | 2.483 | 2.056 | 2.270 |
| 8 | 0.706 | 0.525 | 0.616 | 2.181 | 2.127 | 2.154 |
| 9 | 0.624 | 0.737 | 0.681 | 2.136 | 2.654 | 2.395 |
| 10 | 0.893 | 0.676 | 0.785 | 2.003 | 2.261 | 2.132 |
| Total Average | 0.753 | 0.677 | 0.715 | 2.335 | 2.237 | 2.286 |

| Sample # | Diaper 2 - First Portion Thickness (mm) | | | Diaper 2 - Second Portion Thickness (mm) | | |
|---|---|---|---|---|---|---|
| | Left Flap | Right Flap | Left/Right Average | Left Flap | Right Flap | Left/Right Average |
| 1 | 0.635 | 0.959 | 0.797 | 1.866 | 1.885 | 1.876 |
| 2 | 0.715 | 0.656 | 0.686 | 1.737 | 1.730 | 1.734 |
| 3 | 0.570 | 0.792 | 0.681 | 1.743 | 1.723 | 1.733 |
| 4 | 0.941 | 0.834 | 0.888 | 1.668 | 1.768 | 1.718 |
| 5 | 0.922 | 0.731 | 0.827 | 2.001 | 1.740 | 1.871 |
| 6 | 0.763 | 0.695 | 0.729 | 1.954 | 1.892 | 1.923 |
| 7 | 0.736 | 0.700 | 0.718 | 1.943 | 1.808 | 1.876 |
| 8 | 0.716 | 0.792 | 0.754 | 2.013 | 1.659 | 1.836 |
| 9 | 0.727 | 0.716 | 0.722 | 1.967 | 2.013 | 1.990 |
| 10 | 0.919 | 0.690 | 0.805 | 1.737 | 1.555 | 1.646 |
| Total Average | 0.764 | 0.757 | 0.760 | 1.863 | 1.777 | 1.820 |

TABLE 3

| Sample # | Diaper 1 - First Portion Elongation Force (gm-force) | | | Diaper 1 - Second Portion Elongation Force (gm-force) | | |
|---|---|---|---|---|---|---|
| | Left Flap | Right Flap | Left/Right Average | Left Flap | Right Flap | Left/Right Average |
| 1 | 100.8 | 79.3 | 90.050 | 284.9 | 292.7 | 288.800 |
| 2 | 77.7 | 74.1 | 75.900 | 260.5 | 253.3 | 256.900 |
| 3 | 69.6 | 74.4 | 72.000 | 266.3 | 179.8 | 223.050 |
| 4 | 68.2 | 71.4 | 69.800 | 205 | 281.7 | 243.350 |
| 5 | 79 | 77.7 | 78.350 | 292.7 | 250.9 | 271.800 |
| 6 | 75.6 | 556.9 | 316.250 | 281.3 | 434.6 | 357.950 |
| 7 | 70.3 | 70.4 | 70.350 | 322.3 | 299.8 | 311.050 |
| 8 | 77.6 | 87 | 82.300 | 306.3 | 272.3 | 289.300 |
| 9 | 76 | 71.2 | 73.600 | 238.1 | 375.2 | 306.650 |
| 10 | 69.5 | 76 | 72.750 | 279.7 | 216.9 | 248.300 |
| Total Average | 76.430 | 123.840 | 100.135 | 273.710 | 285.720 | 279.715 |

| Sample # | Diaper 2 - First Portion Elongation Force (gm-force) | | | Diaper 2 - Second Portion Elongation Force (gm-force) | | |
|---|---|---|---|---|---|---|
| | Left Flap | Right Flap | Left/Right Average | Left Flap | Right Flap | Left/Right Average |
| 1 | 72.4 | 84.9 | 78.650 | 166.3 | 173.3 | 169.800 |
| 2 | 79.3 | 75.3 | 77.300 | 159.7 | 98.8 | 129.250 |
| 3 | 71.5 | 113.9 | 92.700 | 237.6 | 103.4 | 170.500 |
| 4 | 81.7 | 893 | 487.350 | 106.2 | 89.8 | 98.000 |
| 5 | 68.9 | 75.6 | 72.250 | 117.9 | 126.9 | 122.400 |
| 6 | 79.1 | 71.3 | 75.200 | 165.4 | 89.2 | 127.300 |
| 7 | 64.6 | 68.9 | 66.750 | 166.7 | 145.5 | 156.100 |
| 8 | 65.3 | 75.3 | 70.300 | 157.5 | 102.8 | 130.150 |
| 9 | 64.7 | 71.4 | 68.050 | 196.7 | 84.9 | 140.800 |
| 10 | 72 | 74.5 | 73.250 | 183.2 | 95.8 | 139.500 |
| Total Average | 71.950 | 160.410 | 116.180 | 165.720 | 111.040 | 138.380 |

TABLE 4

| Sample # | Diaper 1 - First Portion Coefficient of Friction | | Diaper 1 - Second Portion Coefficient of Friction | |
|---|---|---|---|---|
| | Right Flap (MIU) | Right Flap (MMD) | Right Flap (MIU) | Right Flap (MMD) |
| 1 | 0.631 | 0.0104 | 0.769 | 0.021 |
| 2 | 0.596 | 0.0092 | 0.73 | 0.0267 |
| 3 | 0.614 | 0.0091 | 0.808 | 0.0279 |
| 4 | 0.638 | 0.0098 | 0.694 | 0.0357 |
| 5 | 0.615 | 0.01 | 0.868 | 0.0204 |
| 6 | 0.582 | 0.0097 | 0.815 | 0.0299 |
| 7 | 0.613 | 0.0107 | 0.798 | 0.0203 |
| 8 | 0.618 | 0.0094 | 0.817 | 0.0345 |
| 9 | 0.629 | 0.0097 | 0.756 | 0.0551 |
| 10 | 0.563 | 0.0084 | 0.836 | 0.0392 |
| Total Average | 0.610 | 0.010 | 0.789 | 0.031 |

| Sample # | Diaper 2 - First Portion Coefficient of Friction | | Diaper 2 - Second Portion Coefficient of Friction | |
|---|---|---|---|---|
| | Right Flap (MIU) | Right Flap (MMD) | Right Flap (MIU) | Right Flap (MMD) |
| 1 | 0.586 | 0.0083 | 0.795 | 0.0211 |
| 2 | 0.594 | 0.0108 | 0.65 | 0.0315 |
| 3 | 0.575 | 0.0092 | 0.785 | 0.0399 |
| 4 | 0.553 | 0.0114 | 0.726 | 0.0271 |
| 5 | 0.621 | 0.0116 | 0.729 | 0.0297 |
| 6 | 0.597 | 0.0095 | 0.775 | 0.0322 |
| 7 | 0.583 | 0.0104 | 0.825 | 0.0342 |
| 8 | 0.581 | 0.009 | 0.847 | 0.0265 |
| 9 | 0.581 | 0.0092 | 0.726 | 0.0345 |
| 10 | 0.618 | 0.0113 | 0.707 | 0.0348 |
| Total Average | 0.589 | 0.010 | 0.757 | 0.031 |

TABLE 5

| Sample # | Diaper 1 - First Portion - Width Gurley Stiffness (mg-force) | | | Diaper 1 - Second Portion - Width Gurley Stiffness (mg-force) | | |
|---|---|---|---|---|---|---|
| | Left Flap | Right Flap | Left/Right Average | Left Flap | Right Flap | Left/Right Average |
| 1 | 2.22 | 2.64 | 2.433 | 111.20 | 113.98 | 112.590 |
| 2 | 5.14 | 2.64 | 3.892 | 122.32 | 116.76 | 119.540 |
| 3 | 2.36 | 1.53 | 1.946 | 100.08 | 113.98 | 107.030 |
| 4 | 14.46 | 2.09 | 8.271 | 125.10 | 111.20 | 118.150 |
| 5 | 5.98 | 4.73 | 5.352 | 122.32 | 97.30 | 109.810 |
| 6 | 4.73 | 3.75 | 4.240 | 125.10 | 141.78 | 133.440 |
| 7 | 3.75 | 2.78 | 3.267 | 130.66 | 83.40 | 107.030 |
| 8 | 3.75 | 7.65 | 5.699 | 97.30 | 91.74 | 94.520 |
| 9 | 4.87 | 5.98 | 5.421 | 136.22 | 130.66 | 133.440 |
| 10 | 2.92 | 3.61 | 3.267 | 100.08 | 113.98 | 107.030 |
| Total Average | 5.02 | 3.74 | 4.38 | 117.04 | 111.48 | 114.26 |

| Sample # | Diaper 2 - First Portion - Width Gurley Stiffness (mg-force) | | | Diaper 2 - Second Portion - Width Gurley Stiffness (mg-force) | | |
|---|---|---|---|---|---|---|
| | Left Flap | Right Flap | Left/Right Average | Left Flap | Right Flap | Left/Right Average |
| 1 | 3.34 | 5.70 | 4.52 | 161.24 | 183.48 | 172.36 |
| 2 | 3.89 | 10.43 | 7.16 | 130.66 | 150.12 | 140.39 |
| 3 | 3.89 | 6.12 | 5.00 | 164.02 | 164.02 | 164.02 |
| 4 | 9.17 | 6.53 | 7.85 | 125.10 | 155.68 | 140.39 |
| 5 | 7.23 | 4.17 | 5.70 | 116.76 | 144.56 | 130.66 |
| 6 | 6.39 | 2.92 | 4.66 | 144.56 | 191.82 | 168.19 |
| 7 | 4.87 | 3.20 | 4.03 | 130.66 | 133.44 | 132.05 |
| 8 | 3.48 | 11.40 | 7.44 | 166.80 | 161.24 | 164.02 |
| 9 | 5.28 | 4.03 | 4.66 | 169.58 | 158.46 | 164.02 |
| 10 | 4.73 | 5.70 | 5.21 | 119.54 | 127.88 | 123.71 |
| Total Average | 5.23 | 6.02 | 5.62 | 142.89 | 157.07 | 149.98 |

TABLE 6

| Sample # | Diaper 1 - First Portion - Length Gurley Stiffness (mg-force) | | | Diaper 1 - Second Portion - Length Gurley Stiffness (mg-force) | | |
|---|---|---|---|---|---|---|
| | Left Flap | Right Flap | Left/Right Average | Left Flap | Right Flap | Left/Right Average |
| 1 | 6.12 | 2.64 | 4.379 | 31.41 | 29.47 | 30.441 |
| 2 | 3.20 | 4.17 | 3.684 | 32.53 | 28.91 | 30.719 |
| 3 | 2.92 | 5.14 | 4.031 | 26.97 | 35.86 | 31.414 |
| 4 | 3.61 | 4.73 | 4.170 | 26.69 | 30.30 | 28.495 |
| 5 | 6.12 | 4.31 | 5.213 | 27.52 | 29.19 | 28.356 |
| 6 | 4.59 | 3.48 | 4.031 | 31.41 | 33.64 | 32.526 |
| 7 | 4.59 | 4.45 | 4.518 | 26.41 | 26.69 | 26.549 |
| 8 | 3.75 | 3.20 | 3.475 | 29.47 | 26.97 | 28.217 |
| 9 | 3.34 | 5.56 | 4.448 | 31.97 | 33.64 | 32.804 |
| 10 | 3.06 | 3.89 | 3.475 | 28.08 | 28.91 | 28.495 |
| Total Average | 4.13 | 4.16 | 4.14 | 29.25 | 30.36 | 29.80 |

| Sample # | Diaper 2 - First Portion - Length Gurley Stiffness (mg-force) | | | Diaper 2 - Second Portion - Length Gurley Stiffness (mg-force) | | |
|---|---|---|---|---|---|---|
| | Left Flap | Right Flap | Left/Right Average | Left Flap | Right Flap | Left/Right Average |
| 1 | 5.84 | 7.23 | 6.53 | 22.80 | 20.57 | 21.68 |
| 2 | 6.12 | 4.31 | 5.21 | 19.18 | 15.85 | 17.51 |
| 3 | 4.45 | 4.31 | 4.38 | 20.02 | 20.02 | 20.02 |
| 4 | 7.92 | 8.62 | 8.27 | 20.57 | 18.35 | 19.46 |
| 5 | 3.89 | 7.09 | 5.49 | 24.74 | 18.35 | 21.55 |
| 6 | 4.87 | 9.59 | 7.23 | 30.30 | 18.07 | 24.19 |
| 7 | 4.03 | 5.28 | 4.66 | 23.91 | 19.46 | 21.68 |
| 8 | 5.00 | 4.73 | 4.87 | 18.63 | 18.90 | 18.77 |
| 9 | 6.26 | 5.00 | 5.63 | 22.80 | 17.79 | 20.29 |
| 10 | 8.62 | 5.70 | 7.16 | 19.46 | 20.57 | 20.02 |
| Total Average | 5.70 | 6.19 | 5.94 | 22.24 | 18.79 | 20.52 |

As can be seen from the foregoing description of the absorbent articles according to the present disclosure, a product can be produced which is capable of effectively controlling the spread of BM due to the improved properties of the BM containment flaps due to the change in the properties of the second portions 57 as compared to the first portions of the containment flaps 50, 52.

EMBODIMENTS

Embodiment 1. An absorbent article comprising a chassis having a front end section with a front waist region including a front waist edge and a rear end section having a rear waist region including a rear waist edge, said front waist region and rear waist region being joined by a crotch region, said chassis including an absorbent body, said chassis further including a body facing surface, said article defining a longitudinal axis, a lateral axis located midway between said front waist edge and said rear waist edge, said article further defining a vertical axis;

a pair of containment flaps attached to said body facing surface of said chassis, each of said pair of containment flaps having a proximal edge adjacent and attached to said body facing surface of said chassis and a distal edge joined to said proximal edge by a medial section, each said containment flaps defining a length and having a first end and a second end, said first end being located in said front waist region and said second end being located in said rear waist region, each of said containment flaps having a first portion at least a portion of which is located in said front waist region of said article and a second portion at least a portion of which is located in said rear waist region of said article, each of said containment flaps having at least one property with said at least one property in said second section being different from said at least one property in said first portion of said same containment flap.

Embodiment 2. The absorbent article of embodiment 1 wherein said at least one property is basis weight, said second portion having a higher basis weight than said first portion.

Embodiment 3. The absorbent article of embodiment 1 wherein said at least one property is elongation force, said second portion having a greater elongation force in a direction generally parallel to said longitudinal axis than said first portion.

Embodiment 4. The absorbent article of embodiment 2 wherein said at least one property also includes elongation force, said second portion having a greater elongation force in a direction generally parallel to said longitudinal axis than said first portion.

Embodiment 5. The absorbent article of embodiment 4 wherein said elongation force of said second section is from about 240 grams force to about 375 grams force.

Embodiment 6. The absorbent article of embodiment 1 wherein said at least one property is bending stiffness, said second portion having a greater bending stiffness than said first portion.

Embodiment 7. The absorbent article of embodiment 6 wherein said bending stiffness of said second portion is from about 80 mg to about 190 mg.

Embodiment 8. The absorbent article of embodiment 1 wherein each of said containment flaps has a flap body facing surface and an opposed flap absorbent facing surface, and further wherein said at least one property is coefficient of friction, said flap body facing surface of said second portion having a higher coefficient of friction than said flap body facing surface of said first portion.

Embodiment 9. The absorbent article of embodiment 8 wherein said coefficient of friction of said flap body facing surface of said second portion is about 15 percent to about 35 percent higher than said coefficient of friction of said flap body facing surface 73 of said first portion.

Embodiment 10. The absorbent article of embodiment 1 wherein said at least one property is containment flap height, said second portion having a greater average containment flap height than said first portion.

Embodiment 11. The absorbent article of embodiment 10 wherein said second portion has an average containment flap height which is from about 5 to about 100 percent higher than the average containment flap height of said first portion.

Embodiment 12. The absorbent article of embodiment 1 wherein said second portion does not extend from said rear waist region past said lateral axis of said absorbent article.

Embodiment 13. The absorbent article of embodiment 1 wherein said article is capable of being folded in half such that said front waist edge is in alignment with said rear waist edge and when said article is folded in such a fashion a transverse fold line is formed in said article, said second portion of each of said containment flaps not extending past said fold line.

Embodiment 14. The absorbent article of embodiment 4 wherein said at least one property also includes coefficient of friction, each of said containment flaps having a flap body facing surface and an opposed flap absorbent facing surface, said flap body facing surface of said second portion having a higher coefficient of friction than said flap body facing surface of said first portion of each of said containment flaps.

Embodiment 15. The absorbent article of embodiment 1 wherein said at least one property is thickness, said second portion having a greater average thickness than said first portion.

Embodiment 16. The absorbent article of embodiment 1 wherein said at least one property causes said second portion to be visually distinct from said first portion.

Embodiment 17. An absorbent article comprising a chassis having a front end section with a front waist region including a front waist edge and a rear end section having a rear waist region including a rear waist edge, said front waist region and rear waist region being joined by a crotch region, said chassis including an absorbent body, said chassis further including a body facing surface, said article defining a longitudinal axis, a lateral axis located midway between said front waist edge and said rear waist edge, said article further defining a vertical axis;

a pair of containment flaps attached to said body facing surface of said chassis, each of said pair of containment flaps having a proximal edge adjacent and attached to said body facing surface of said chassis and a distal edge joined to said proximal edge by a medial section, each said containment flaps defining a length and having a first end and a second end, said first end being located in said front waist region and said second end being located in said rear waist region, each of said containment flaps having a first portion at least a portion of which is located in said front waist region of said article and a second portion at least a portion of which is located in said rear waist region of said article, each of said containment flaps having at least one property with said at least one property in said second section being different from said at least one property in said first portion of said same containment flap, said at least one property including elongation force, said second portion having a greater elongation force in a direction generally parallel to said longitudinal axis than said first portion, said at least one property also including bending stiffness, said second portion having a greater bending stiffness than said first portion, and each of said pair of containment flaps having a flap body facing surface and an opposed flap absorbent facing surface, and further wherein said at least one property further includes coefficient of friction, said flap body facing surface of said second portion of each of said pair of containment flaps having a higher coefficient of friction than said flap body facing surface of said first portion of each of said pair of containment flaps.

Embodiment 18. The absorbent article of embodiment 17 wherein said at least one property also includes basis weight, said second portion having a higher basis weight than said first portion.

Embodiment 19. The absorbent article of embodiment 18 wherein said second portion does not extend from said rear waist region past said lateral axis of said absorbent article.

Embodiment 20. The absorbent article of embodiment 19 wherein said second portion of each of said pair of containment flaps is visually distinct from said first portion of each of said pair of containment flaps.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a chassis having a front end section with a front waist region including a front waist edge and a rear end section having a rear waist region including a rear waist edge, said front waist region and rear waist region being joined by a crotch region, said chassis including an absorbent body, said chassis further including a body facing surface, said article defining a longitudinal axis, a lateral axis located midway between said front waist edge and said rear waist edge, said article further defining a vertical axis;

a pair of containment flaps attached to said body facing surface of said chassis, each of said pair of containment flaps having a proximal edge adjacent and attached to said body facing surface of said chassis and a distal edge joined to said proximal edge by a medial section, each said containment flaps defining a length and having a first end and a second end, said first end being located in said front waist region and said second end being located in said rear waist region, each of said containment flaps having a first portion at least a portion of which is located in said front waist region of said article and a second portion at least a portion of which is located in said rear waist region of said article, the second portion of each containment flap further comprising a secondary material coupled to one of the absorbent facing surface and the body facing surface with the secondary material extending laterally at least partially between the proximal edge of the containment flap and the distal edge of the containment flap and longitudinally in a continuous manner between the rear waist region and the crotch region and having a first end edge forming a juncture between the containment flap first portion and the containment flap second portion, the juncture located within the crotch region, the secondary material imparting the second portion of each of said containment flaps one or more properties of stiffness, thickness, height, basis weight, and coefficient of friction that is different from said one or more properties in said first portion of said same containment flap.

2. The absorbent article of claim 1 wherein said at least one property is basis weight, said second portion having a higher basis weight than said first portion.

3. The absorbent article of claim 1 wherein said at least one property is elongation force, said second portion having a greater elongation force in a direction generally parallel to said longitudinal axis than said first portion.

4. The absorbent article of claim 2 wherein said at least one property also includes elongation force, said second portion having a greater elongation force in a direction generally parallel to said longitudinal axis than said first portion.

5. The absorbent article of claim 4 wherein said elongation force of said second section is from about 240 grams force to about 375 grams force.

6. The absorbent article of claim 1 wherein said at least one property is bending stiffness, said second portion having a greater bending stiffness than said first portion.

7. The absorbent article of claim 6 wherein said bending stiffness of said second portion is from about 80 mg to about 190 mg.

8. The absorbent article of claim 1 wherein each of said containment flaps has a flap body facing surface and an opposed flap absorbent facing surface, and further wherein said at least one property is coefficient of friction, said flap body facing surface of said second portion having a higher coefficient of friction than said flap body facing surface of said first portion.

9. The absorbent article of claim 8 wherein said coefficient of friction of said flap body facing surface of said second portion is about 15 percent to about 35 percent higher than said coefficient of friction of said flap body facing surface of said first portion.

10. The absorbent article of claim 1 wherein said at least one property is containment flap height, said second portion having a greater average containment flap height than said first portion.

11. The absorbent article of claim 10 wherein said second portion has an average containment flap height which is from about 5 to about 100 percent higher than the average containment flap height of said first portion.

12. The absorbent article of claim 1 wherein said juncture is located in the crotch region and is disposed closer to the rear waist edge than the front waist edge.

13. The absorbent article of claim 1 wherein said article is capable of being folded such that said front waist region edge is disposed in an overlapping fashion with said rear waist region edge and when said article is folded in such a fashion a transverse fold line is formed in said article, said juncture is disposed closer to the rear waist edge than said fold line.

14. The absorbent article of claim 4 wherein said at least one property also includes coefficient of friction, each of said containment flaps having a flap body facing surface and an opposed flap absorbent facing surface, said flap body facing surface of said second portion having a higher coefficient of friction than said flap body facing surface of said first portion of each of said containment flaps.

15. The absorbent article of claim 1 wherein said at least one property is thickness, said second portion having a greater average thickness than said first portion.

16. The absorbent article of claim 1 wherein said at least one property causes said second portion to be visually distinct from said first portion.

17. An absorbent article comprising a chassis having a front end section with a front waist region including a front waist edge and a rear end section having a rear waist region including a rear waist edge, said front waist region and rear waist region being joined by a crotch region, said chassis including an absorbent body, said chassis further including a body facing surface, said article defining a longitudinal axis, a lateral axis located midway between said front waist edge and said rear waist edge, said article further defining a vertical axis;

a pair of containment flaps attached to said body facing surface of said chassis, each of said pair of containment flaps having a proximal edge adjacent and attached to said body facing surface of said chassis and a distal edge joined to said proximal edge by a medial section, each said containment flaps defining a length and having a first end and a second end, said first end being located in said front waist region and said second end being located in said rear waist region, each of said containment flaps having a first portion at least a portion of which is located in said front waist region of said article and a second portion extending in a continuous manner between said rear waist region and said crotch region of said article, each of said containment flaps having at least one property with said at least one property in throughout said second section being different from said at least one property in throughout said first portion of said same containment flap, said at least one property including elongation force, said second portion having a greater elongation force in a direction generally parallel to said longitudinal axis than said first portion, and said at least one property also including bending stiffness, said second portion having a greater bending stiffness than said first portion.

18. The absorbent article of claim 17 wherein said at least one property also includes basis weight, said second portion having a higher basis weight than said first portion.

19. The absorbent article of claim 18 wherein said second portion does not extend from said rear waist region past said lateral axis of said absorbent article.

20. The absorbent article of claim 19 wherein said second portion of each of said pair of containment flaps is visually distinct from said first portion of each of said pair of containment flaps.

* * * * *